(12) United States Patent
Misra et al.

(10) Patent No.: US 6,759,529 B1
(45) Date of Patent: Jul. 6, 2004

(54) PLANT-GENE PROMOTER AND METHODS OF USING THE SAME

(75) Inventors: Santosh Misra, Victoria (CA); Malinee Chattai, Bangkok (TH)

(73) Assignee: University of Victoria Innovation and Development Corporation, Victoria (CA)

( * ) Notice: Subject to any disclaimer, the term of this patent is extended or adjusted under 35 U.S.C. 154(b) by 0 days.

(21) Appl. No.: 09/641,540

(22) Filed: Aug. 18, 2000

(51) Int. Cl.$^7$ .................. C07H 21/02; C07H 21/04; C12P 21/06; C12N 15/00; C12N 15/09; C12N 15/63; C12N 15/70; C12N 5/04; C12N 5/10

(52) U.S. Cl. .................. 536/24.1; 435/6; 435/69.1; 435/320.1; 435/419; 800/287

(58) Field of Search .................. 536/24.1; 435/69.1, 435/320.1, 419; 800/287

(56) References Cited

PUBLICATIONS

Vetten, N. C. et al., "Transcriptional regulation of environmentally inducible genes in plants by an evolutionary conserved family of G–box binding factors", Int. J. Biochem., vol. 9, pp. 1055–1068 (1994).*

Chatthai, M., "Molecular characterization and regulation of embryogenesis–associated genes in Douglas–fir (*Pseudotsuga menziesii* [Mirb.] Franco)", Ph. D. Dissertation, University of Victoria, pp. 123–178 (1999).*

Chattahi, "Molecular Characterization and Regulation of Embryogenesis–Associated Genes in Douglas–Fir (*Psuedotsuga menziesii* [MIRB.] Franco)," pp. 1–84, 1999. Incomplete (Relevant Information Dup. 156→).

Chattahi, *Plant Mol. Biol.* 34:243–254, 1997.

* cited by examiner

*Primary Examiner*—Jeffrey Fredman
*Assistant Examiner*—Teresa Strzelecka
(74) *Attorney, Agent, or Firm*—Klarquist Sparkman, LLP

(57) ABSTRACT

The invention provides promoters from Douglas-fir genes encoding metallothionein-like proteins. Also provided are deletions and variants of such promoters. The promoters are useful for, among other things, directing developmental-specific expression of transgenes.

12 Claims, 3 Drawing Sheets

```
-856 cccctagagagttctgaatgatccagaaagtttagtatgaaaatgagcaatcccacaattcttccaaaaaaaaatgaagggataagggatggtttggatg
          ERE
-756 gcaagggatttcaacattggaagatcctttgagtttttatttggaagatgatttgaagttttcactaaataattgatatgatgataatgacaaagataa
          A/T rich                                          ERE          ERE
-656 tagttactacattgaaaccaatttagtttaataatttcttaaaaaaatataagccccaatctaattttgaaatttgaaagatatatgattattcaacct
                                                    E-box
-556 aaagagataagataagatccaactccttcgagtgcttttggtgacataaatatagggtttatccatttgcgacgatgatatacaatggacgatccagaaa -456 gttccctataaaatgaggatttcacgaaagaatcccattgtacggctcaggatttcgacattgaaagatccattaatgagatgcttggcagggctcagc
          MRE
-356 actgaatgcgccctgtcccacttcgaagagattccaccggccgtcttgcgcctttcattgttgtttggattctcatggcgggtctgtggacaatacctg
                                                                      ACGT        ACGT
-256 cagcttcggccatctataattgccacggaaggctgctcttcttctcaacaatcaaagcaaaagcaaagctattctgtgtattgcaatttccaacgttga
                                                ACGT
-156 aagatccattattgagatgcctgtcccacttcgatgagattccaccacgtgtcttgcgcctttcattgttgtttggattctaatggcgggtctgtgggc -56 catccttcagcttcggccacttataaatgccacggaaggctgctcttcttctcaacaatcaaagcaaaatcagagagaattctgtgtattgcggtttcc.
                                                                    +1                    EcoR I
 45 cgacgtttgtatcagttttcttgtgtttgttaacgatctgcaaacATGTCTTCTGACGGCAAAGACTGTGGCTGTGCCGACCCAACCCAATGCGAgtaagt
                                                 M  S  S  D  G  K  D  C  G  C  A  D  P  T  Q  C  D
145 cctctctttatttcaggtttcctcctcacctcaattcattatcacgatcctgtaaattattcagtttttaatggctgatatcagtttttgtgtgtgtta 245 ctgctattaataatggcagCAAGAAGGGCAACTCCTTGGGAGTGGAGATGGTTGAAACCAGCTACGACTACAACATGAACATGAGgtgagttttgggcat
                         K  K  G  N  S  L  G  V  E  M  V  E  T  S  Y  D  Y  N  M  N  M  S
345 tatttgttttaaagattgaaacatgcaatgaatctaatctggttttccaatttgcgtctgcagCTTCGGCTTCGACTACGAGATGGAAACTGTGGCTGCT
                                                                   F  G  F  D  Y  E  M  E  T  V  A  A
445 GAGAACGGCTGCAAATCCGGAGCAAGCTCCAAGTACTCCAACCGCTGCAACTGAattatggaggacataaaagacttgctacatattatatataragaaa
     E  N  G  C  K  S  G  A  S  S  K  Y  S  N  R  C  N  *
545 ataagtgttgtgtgatgctgagggatctcacgatgttattgatgtcatgtctggtgttgttattctacccgtgtcactgttgtaatgccggccttcctct
645 tttattaactatgatatgatattttagagtaatttgtgttatatgattatgtgcttttctatcttattaactatgttattagtccctgctttgaggagtt
745 ggcagggactctatgaaagggcttgcaatcgtttcattagtcctgcacgcaaatcaaagatatatattttattagtcctgcacgcaaattaaagatatt
845 ttttttttgaatgtagggactgtatgaaagggcttgtagtggtttcattagtcctgcacacaaaccaaagatatatatttcacatgtatcctaagtctt
945 tactcaccttaaagttattatgacatgtatactaagtttaaagcactatgtcacacgtatctagttagttttactatttaccatcaaaagttgagtcttg
1045 ttggcctggtatcgaggcaaaggcaagaaagggcagctatacttcatacatttgaaatattaattcatggtatcgaacatatttgaaatattaattcat
1145 ggtattgaacatatgttatactttttgaataatgctaacaatcctcgtagcattacttcccttacatttagtatgattgcaaatcaaaaattatagtacg
1245 attgtaactaaaaaattatattctatcaatgcatgtagcacaagccgccttcacacctgccaagaaacttctgcatgcaacacatgccttcttcacacct
1345 accaagaaacttctaggtgttaatttgctcaagctagttctacgtgtagatttacacaagctgaaacaatgcagtgtgcatgccttatgttaacacctgc
1445 ctagaacttctactaggaattc
         EcoR I
```

Figure 1

SEQUENCE LISTING

<160> NUMBER OF SEQ ID NOS: 28

<210> SEQ ID NO 1
<211> LENGTH: 6
<212> TYPE: DNA
<213> ORGANISM: Artificial Sequence
<220> FEATURE:
<221> NAME/KEY: variation
<222> LOCATION: (3)..(4)
<223> OTHER INFORMATION: N = A, C, G, or T
<223> OTHER INFORMATION: Description of Artificial Sequence: PROMOTER
      ELEMENT

<400> SEQUENCE: 1 canntg                                                                    6

<210> SEQ ID NO 2
<211> LENGTH: 6
<212> TYPE: DNA
<213> ORGANISM: Artificial Sequence
<220> FEATURE:
<223> OTHER INFORMATION: Description of Artificial Sequence: PROMOTER
      ELEMENT

<400> SEQUENCE: 2 gcatgc                                                                    6

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: PROMOTER
      ELEMENT

<400> SEQUENCE: 3
aaaaattaat atttaatgtt aatattaat                                          29

<210> SEQ ID NO 4
<211> LENGTH: 4
<212> TYPE: DNA
<213> ORGANISM: Artificial Sequence
<220> FEATURE:
<223> OTHER INFORMATION: Description of Artificial Sequence: PROMOTER
      ELEMENT

<400> SEQUENCE: 4 acgt                                                                      4

<210> SEQ ID NO 5
<211> LENGTH: 9
<212> TYPE: DNA
<213> ORGANISM: Artificial Sequence

```
<220> FEATURE:
<221> NAME/KEY: variation
<222> LOCATION: (3)..(4)
<223> OTHER INFORMATION: N = A, C, G, and T
<223> OTHER INFORMATION: Description of Artificial Sequence: PROMOTER
      ELEMENT

<400> SEQUENCE: 5 ttnntcatc                                                                 9

<210> SEQ ID NO 6
<211> LENGTH: 13
<212> TYPE: DNA
<213> ORGANISM: Artificial Sequence
<220> FEATURE:
<223> OTHER INFORMATION: Description of Artificial Sequence: PROMOTER
      ELEMENT

<400> SEQUENCE: 6
aagattcctc taa                                                           13

<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence: PROMOTER
      ELEMENT

<400> SEQUENCE: 7
gttgttgaga                                                               10

<210> SEQ ID NO 8
<211> LENGTH: 4
<212> TYPE: DNA
<213> ORGANISM: Artificial Sequence
<220> FEATURE:
<223> OTHER INFORMATION: Description of Artificial Sequence: PROMOTER
      ELEMENT

<400> SEQUENCE: 8 tata                                                                      4

<210> SEQ ID NO 9
<211> LENGTH: 4
<212> TYPE: DNA
<213> ORGANISM: Artificial Sequence
<220> FEATURE:
<223> OTHER INFORMATION: Description of Artificial Sequence: PROMOTER
      ELEMENT

<400> SEQUENCE: 9 caat                                                                      4

<210> SEQ ID NO 10
<211> LENGTH: 2322
<212> TYPE: DNA
<213> ORGANISM: Pseudotsuga menziesii

<400> SEQUENCE: 10
cccctagaga gttctgaatg atccagaaag tttagtatga aaatgagcaa tcccacaatt         60
cttccaaaaa aaaatgaagg gataagggat ggtttggatg gcaagggatt tcaacattgg        120
aagatccttt gaggttttta tttggaagat gatttgaagt tttcactaaa taattgatat        180
gatgataatg acaaagataa tagttactac attgaaacca attttagttt aataatttct        240
```

-continued

| | |
|---|---|
| taaaaaaata taagccccaa tctaattttg aaatttgaaa gatatatgat tattcaacct | 300 |
| aaagagataa gataagatcc aactccttcg agtgcttttg gtgacataaa tatagggttt | 360 |
| atccatttgc gacgatgata tacaatggac gatccagaaa gttccctata aaatgaggat | 420 |
| ttcacgaaag aatcccattg tacggctcag gatttcgaca ttgaaagatc cattaatgag | 480 |
| atgcttggca ggggctcagc actgaatgcg ccctgtccca cttcgaagag attccaccgg | 540 |
| ccgtcttgcg cctttcattg ttgttttgga ttctcatggc gggtctgtgg acaatacctg | 600 |
| cagcttcggc catctataat tgccacggaa ggctgctctt cttctcaaca atcaaagcaa | 660 |
| aagcaaagct tattctgtgt attgcaattt ccaacgttga agatccatt attgagatgc | 720 |
| cctgtcccac ttcgatgaga ttccaccacg tgtcttgcgc cttcattgt tgtttggatt | 780 |
| ctaatggcgg gtctgtgggc catacctca gcttcggcca cttataaatg ccacggaagg | 840 |
| ctgctcttct tctcaacaat caaagcaaaa tcagagagaa ttctgtgtat tgcggtttcc | 900 |
| cgacgtttgt atcagtttct tgtgtttgtt aacgatctgc aaacatgtct tctgacggca | 960 |
| aagactgtgg ctgtgccgac ccaacccaat gcgagtaagt cctctcttta tttcaggttt | 1020 |
| cctcctcacc tcaattcatt atcacgatcc tgtaaattat ttcagttttt aatggctgat | 1080 |
| atcagttttt gtgtgtgtta ctgctattaa taatggcagc aagaagggca actccttggg | 1140 |
| agtggagatg gttgaaacca gctacgacta caacatgaac atgaggtgag ttttgggcat | 1200 |
| tatttgtttt aaagattgaa acatgcaatg aatctaatct ggtttccaat tttgcgtctg | 1260 |
| cagcttcggc ttcgactacg agatggaaac tgtggctgct gagaacggct gcaaatccgg | 1320 |
| agcaagctcc aagtactcca accgctgcaa ctgaattatg gaggacataa aagacttgct | 1380 |
| acatattata tatatagaaa ataagtgttg tgtgatgctg agggatctca cgatgttatt | 1440 |
| gatgtcatgt ctggtgttgt tattctaccc gtgtcactgt tgtaatgccg gccttcctct | 1500 |
| tttattaact atgatatgat attttagagt aatttgtgtt atatgattat gtgcttttct | 1560 |
| atcttattaa ctatgttatt agtccctgct ttgaggagtt ggcagggact ctatgaaagg | 1620 |
| gcttgcaatc gtttcattag tcctgcacgc aaatcaaaga tatatatttt tattagtcct | 1680 |
| gcacgcaaat taaagatatt ttttttttg aatgtaggga ctgtatgaaa gggcttgtag | 1740 |
| tggtttcatt agtcctgtac acaaaccaaa gatatatatt tcacatgtat cctaagtctt | 1800 |
| tactcacctt aaagttatta tgacatgtat actaagttta aagcactatg tcacacgtat | 1860 |
| ctagttagtt ttactattta ccatcaaaag ttgagtcttg ttggcctggt atcgaggcaa | 1920 |
| aggcaagaaa gggcagctat actttcatac atttgaaata ttaattcatg gtatcgaaca | 1980 |
| tatttgaaat attaattcat ggtattgaac atatgttata cttttttgaat aatgctaaca | 2040 |
| atcctcgtag cattacttcc cttacattta gtatgattgc aaatcaaaaa ttatagtatg | 2100 |
| attgtaacta aaaaattata ttctatcaat gcatgtagca caagccgcct tcacacctgc | 2160 |
| caagaaactt ctgcatgcaa cacatgcctt cttcacacct accaagaaac ttctaggtgt | 2220 |
| taatttgctc aagctagttc tacgtgtaga tttacacaag ctgaaacaat gcagtgtgca | 2280 |
| tgccttatgt taacacctgc ctagaacttc tactaggaat tc | 2322 |

<210> SEQ ID NO 11
<211> LENGTH: 207
<212> TYPE: DNA
<213> ORGANISM: Pseudotsuga menziesii

<400> SEQUENCE: 11

| | |
|---|---|
| atgtcttctg acggcaaaga ctgtggctgt gccgacccaa cccaatgcga caagaagggc | 60 |

```
aactccttgg gagtggagat ggttgaaacc agctacgact acaacatgaa catgagcttc      120
ggcttcgact acgagatgga aactgtggct gctgagaacg gctgcaaatc cggagcaagc      180
tccaagtact ccaaccgctg caactga                                         207
```

<210> SEQ ID NO 12
<211> LENGTH: 968
<212> TYPE: DNA
<213> ORGANISM: Pseudotsuga menziesii
<220> FEATURE:
<221> NAME/KEY: promoter
<222> LOCATION: (1)..(856)

<400> SEQUENCE: 12

```
attatggagg acataaaaga cttgctacat attatatata tagaaaataa gtgttgtgtg       60
atgctgaggg atctcacgat gttattgatg tcatgtctgg tgttgttatt ctacccgtgt      120
cactgttgta atgccggcct tcctctttta ttaactatga tatgatattt tagagtaatt      180
tgtgttatat gattatgtgc ttttctatct tattaactat gttattagtc cctgctttga      240
ggagttggca gggactctat gaaagggctt gcaatcgttt cattagtcct gcacgcaaat      300
caaagatata tattttttatt agtcctgcac gcaaattaaa gatattttt ttttgaatg       360 tagggactgt atgaaagggc ttgtagtggt tcattagtc ctgtacacaa accaaagata       420
tatatttcac atgtatccta agtctttact caccttaaag ttattatgac atgtatacta      480
agtttaaagc actatgtcac acgtatctag ttagttttac tatttaccat caaaagttga      540
gtcttgttgg cctggtatcg aggcaaaggc aagaaagggc agctatactt tcatacattt      600
gaaatattaa ttcatggtat cgaacatatt tgaaatatta attcatggta ttgaacatat      660
gttatacttt ttgaataatg ctaacaatcc tcgtagcatt acttcccta catttagtat       720 gattgcaaat caaaaattat agtatgattg taactaaaaa attatattct atcaatgcat      780
gtagcacaag ccgccttcac acctgccaag aaacttctgc atgcaacaca tgccttcttc      840
acacctacca agaaacttct aggtgttaat ttgctcaagc tagttctacg tgtagattta      900
cacaagctga aacaatgcag tgtgcatgcc ttatgttaac acctgcctag aacttctact      960
aggaattc                                                              968
```

<210> SEQ ID NO 13
<211> LENGTH: 68
<212> TYPE: PRT
<213> ORGANISM: Pseudotsuga menziesii

<400> SEQUENCE: 13

```
Met Ser Ser Asp Gly Lys Asp Cys Gly Cys Ala Asp Pro Thr Gln Cys
  1               5                  10                  15

Asp Lys Lys Gly Asn Ser Leu Gly Val Glu Met Val Glu Thr Ser Tyr
             20                  25                  30

Asp Tyr Asn Met Asn Met Ser Phe Gly Phe Asp Tyr Glu Met Glu Thr
         35                  40                  45

Val Ala Ala Glu Asn Gly Cys Lys Ser Gly Ala Ser Ser Lys Tyr Ser
     50                  55                  60

Asn Arg Cys Asn
 65
```

<210> SEQ ID NO 14
<211> LENGTH: 9
<212> TYPE: DNA

-continued

<213> ORGANISM: Artificial Sequence
<220> FEATURE:
<223> OTHER INFORMATION: Description of Artificial Sequence: PROMOTER
      ELEMENT

<400> SEQUENCE: 14 ttcgtcatc                                                                 9

<210> SEQ ID NO 15
<211> LENGTH: 9
<212> TYPE: DNA
<213> ORGANISM: Artificial Sequence
<220> FEATURE:
<223> OTHER INFORMATION: Description of Artificial Sequence: PROMOTER
      ELEMENT

<400> SEQUENCE: 15 tttatcatc                                                                 9

<210> SEQ ID NO 16
<211> LENGTH: 13
<212> TYPE: DNA
<213> ORGANISM: Artificial Sequence
<220> FEATURE:
<223> OTHER INFORMATION: Description of Artificial Sequence: PROMOTER
      ELEMENT

<400> SEQUENCE: 16
cgaaagagca atg                                                           13

<210> SEQ ID NO 17
<211> LENGTH: 853
<212> TYPE: DNA
<213> ORGANISM: Pseudotsuga menziesii

<400> SEQUENCE: 17
cccctagaga gttctgaatg atccagaaag tttagtatga aaatgagcaa tcccacaatt         60
cttccaaaaa aaaatgaagg gataagggat ggtttggatg gcaagggatt tcaacattgg        120
aagatccttt gaggttttta tttggaagat gatttgaagt tttcactaaa taattgatat        180
gatgataatg acaaagataa tagttactac attgaaacca attttagttt aataatttct        240
taaaaaaata taagccccaa tctaattttg aaatttgaaa gatatatgat tattcaacct        300
aaagagataa gataagatcc aactccttcg agtgcttttg gtgacataaa tatagggttt        360
atccatttgc gacgatgata tacaatggac gatccagaaa gttccctata aaatgaggat        420
ttcacgaaag aatcccattg tacggctcag gatttcgaca ttgaaagatc cattaatgag        480
atgcttggca ggggctcagc actgaatgcg ccctgtccca cttcgaagag attccaccgg        540
ccgtcttgcg cctttcattg ttgttttgga ttctcatggc gggtctgtgg acaatacctg        600
cagcttcggc catctataat tgccacggaa ggctgctctt cttctcaaca atcaaagcaa        660
aagcaaagct tattctgtgt attgcaattt ccaacgttga agatccatt attgagatgc        720 cctgtcccac ttcgatgaga ttccaccacg tgtcttgcgc ctttcattgt tgtttggatt        780
ctaatggcgg gtctgtgggc cataccttca gcttcggcca cttataaatg ccacggaagg        840
ctgctcttct tct                                                          853

<210> SEQ ID NO 18
<211> LENGTH: 6
<212> TYPE: DNA
<213> ORGANISM: Artificial Sequence
<220> FEATURE:

-continued

```
<223> OTHER INFORMATION: Description of Artificial Sequence: PROMOTER
      ELEMENT

<400> SEQUENCE: 18 aacgtt                                                                    6

<210> SEQ ID NO 19
<211> LENGTH: 6
<212> TYPE: DNA
<213> ORGANISM: Artificial Sequence
<220> FEATURE:
<223> OTHER INFORMATION: Description of Artificial Sequence: PROMOTER
      ELEMENT

<400> SEQUENCE: 19 cacgtg                                                                    6

<210> SEQ ID NO 20
<211> LENGTH: 8
<212> TYPE: DNA
<213> ORGANISM: Artificial Sequence
<220> FEATURE:
<223> OTHER INFORMATION: Description of Artificial Sequence: PROMOTER
      ELEMENT
<221> NAME/KEY: variation
<222> LOCATION: (1)..(8)
<223> OTHER INFORMATION: W = A OR T

<400> SEQUENCE: 20 awttcaaa                                                                  8

<210> SEQ ID NO 21
<211> LENGTH: 7
<212> TYPE: DNA
<213> ORGANISM: Artificial Sequence
<220> FEATURE:
<221> NAME/KEY: variation
<222> LOCATION: (1)..(7)
<223> OTHER INFORMATION: n = a, t, c, or g
<221> NAME/KEY: variation
<222> LOCATION: (1)..(7)
<223> OTHER INFORMATION: r = g or a
<223> OTHER INFORMATION: Description of Artificial Sequence: PROMOTER
      ELEMENT

<400> SEQUENCE: 21 tgcrcnc                                                                   7

<210> SEQ ID NO 22
<211> LENGTH: 944
<212> TYPE: DNA
<213> ORGANISM: Pseudotsuga menziesii

<400> SEQUENCE: 22
cccctagaga gttctgaatg atccagaaag tttagtatga aaatgagcaa tcccacaatt        60
cttccaaaaa aaaatgaagg gataagggat ggtttggatg gcaagggatt tcaacattgg       120
aagatccttt gaggttttta tttggaagat gatttgaagt tttcactaaa taattgatat       180
gatgataatg acaaagataa tagttactac attgaaacca attttagttt aataatttct       240
taaaaaaata taagccccaa tctaattttg aaatttgaaa gatatatgat tattcaacct       300
aaagagataa gataagatcc aactccttcg agtgcttttg gtgacataaa tatagggttt       360
atccatttgc gacgatgata tacaatggac gatccagaaa gttccctata aaatgaggat       420
ttcacgaaag aatcccattg tacggctcag gatttcgaca ttgaaagatc cattaatgag       480
```

```
atgcttggca ggggctcagc actgaatgcg ccctgtccca cttcgaagag attccaccgg    540
ccgtcttgcg cctttcattg ttgttttgga ttctcatggc gggtctgtgg acaatacctg    600
cagcttcggc catctataat tgccacggaa ggctgctctt cttctcaaca atcaaagcaa    660
aagcaaagct tattctgtgt attgcaattt ccaacgttga aagatccatt attgagatgc    720
cctgtcccac ttcgatgaga ttccaccacg tgtcttgcgc cttcattgt tgtttggatt     780 ctaatggcgg gtctgtgggc cataccttca gcttcggcca cttataaatg ccacggaagg    840
ctgctcttct tctcaacaat caaagcaaaa tcagagagaa ttctgtgtat tgcggtttcc    900
cgacgtttgt atcagtttct tgtgtttgtt aacgatctgc aaac                    944
```

<210> SEQ ID NO 23
<211> LENGTH: 765
<212> TYPE: DNA
<213> ORGANISM: Pseudotsuga menziesii

<400> SEQUENCE: 23

```
tgatgataat gacaaagata atagttacta cattgaaacc aattttagtt taataatttc    60
ttaaaaaaat ataagcccca atctaatttt gaaatttgaa agatatatga ttattcaacc   120
taaagagata agataagatc caactccttc gagtgctttt ggtgacataa atatagggtt   180
tatccatttg cgacgatgat atacaatgga cgatccagaa agttccctat aaaatgagga   240
tttcacgaaa gaatcccatt gtacggctca ggatttcgac attgaaagat ccattaatga   300
gatgcttggc aggggctcag cactgaatgc gccctgtccc acttcgaaga gattccaccg   360
gccgtcttgc gcctttcatt gttgtttgg attctcatgg cgggtctgtg acaatacct    420 gcagcttcgg ccatctataa ttgccacgga aggctgctct tcttctcaac atcaaagca    480 aaagcaaagc ttattctgtg tattgcaatt tccaacgttg aaagatccat tattgagatg   540
ccctgtccca cttcgatgag attccaccac gtgtcttgcg cctttcattg ttgtttggat   600
tctaatggcg gtctgtggg ccataccttc agcttcggcc acttataaat gccacggaag    660
gctgctcttc ttctcaacaa tcaaagcaaa atcagagaga attctgtgta ttgcggtttc   720
ccgacgtttg tatcagtttc ttgtgttgt taacgatctg caaac                     765
```

<210> SEQ ID NO 24
<211> LENGTH: 547
<212> TYPE: DNA
<213> ORGANISM: Pseudotsuga menziesii

<400> SEQUENCE: 24

```
aaagttccct ataaaatgag gatttcacga aagaatccca ttgtacggct caggatttcg    60
acattgaaag atccattaat gagatgcttg caggggctc agcactgaat gcgccctgtc    120
ccacttcgaa gagattccac cggccgtctt gcgcctttca ttgttgtttt ggattctcat   180
ggcgggtctg tggacaatac ctgcagcttc ggccatctat aattgccacg gaaggctgct   240
cttcttctca acaatcaaag caaaagcaaa gcttattctg tgtattgcaa tttccaacgt   300
tgaaagatcc attattgaga tgccctgtcc cacttcgatg agattccacc acgtgtcttg   360
cgcctttcat tgttgtttgg attctaatgg cgggtctgtg gccatacct tcagcttcgg    420 ccacttataa atgccacgga aggctgctct tcttctcaac aatcaaagca aaatcagaga   480
gaattctgtg tattgcggtt tcccgacgtt tgtatcagtt tcttgtgttt gttaacgatc   540
tgcaaac                                                             547
```

```
<210> SEQ ID NO 25
<211> LENGTH: 278
<212> TYPE: DNA
<213> ORGANISM: Pseudotsuga menziesii

<400> SEQUENCE: 25
agcttattct gtgtattgca atttccaacg ttgaaagatc cattattgag atgccctgtc      60
ccacttcgat gagattccac cacgtgtctt gcgcctttca ttgttgtttg gattctaatg     120
gcgggtctgt gggccatacc ttcagcttcg gccacttata aatgccacgg aaggctgctc     180
ttcttctcaa caatcaaagc aaaatcagag agaattctgt gtattgcggt ttcccgacgt     240
ttgtatcagt ttcttgtgtt tgttaacgat ctgcaaac                            278

<210> SEQ ID NO 26
<211> LENGTH: 150
<212> TYPE: DNA
<213> ORGANISM: Pseudotsuga menziesii

<400> SEQUENCE: 26
tgtcccactt cgaagagatt ccaccggccg tcttgcgcct ttcattgttg ttttggattc      60
tcatggcggg tctgtggaca atacctgcag cttcggccat ctataattgc cacggaaggc     120
tgctcttctt ctcaacaatc aaagcaaaag                                      150

<210> SEQ ID NO 27
<211> LENGTH: 150
<212> TYPE: DNA
<213> ORGANISM: Pseudotsuga menziesii

<400> SEQUENCE: 27
tgtcccactt cgatgagatt ccaccacgtg tcttgcgcct ttcattgttg tttggattct      60
aatggcgggt ctgtgggcca taccttcagc ttcggccact tataaatgcc acggaaggct     120
gctcttcttc tcaacaatca aagcaaaatc                                      150

<210> SEQ ID NO 28
<211> LENGTH: 19
<212> TYPE: DNA
<213> ORGANISM: Pseudotsuga menziesii

<400> SEQUENCE: 28
attgcaattt ccaacgttg                                                   19
```

PLANT-GENE PROMOTER AND METHODS OF USING THE SAME

FIELD

This invention relates to an isolated plant-gene promoter and to methods for using such a promoter. More specifically, the promoter was obtained from a gene encoding a metallothionein-like protein.

BACKGROUND
Metallothionein-like Genes and Their Expression Patterns

Genes encoding Metallothionein-like proteins (i.e., "metallothionein-like genes" or "MT-like genes") can be categorized into two classes based on the pattern of cysteine distribution within their predicted translation products (Robinson et al., *Biochem. J.* 295:1–10, 1993). Class I MT-like proteins contain two cysteine-rich domains, as found in animal metallothioneins, and class II MT-like proteins include an additional cysteine-rich domain within the protein. Class I MT-like proteins are further classified into three types (types 1–3) distinguished by the characteristics of their cysteine-containing domains. Each type of MT-like protein also has similar amino acid sequences within spacer regions between the cysteine-rich domains.

To date, Arabidopsis is the only plant species in which metallothionein-like genes of all categories (classes I, II, and types 1–3 of of class I) have been identified. The presence of representatives of each category within a single species (e.g., Arabidopsis) or within closely related species (e.g. wheat, barley, and rice) is significant, as it suggests that plant MT-like proteins may have distinct functions in relation to their structure, patterns of expression, and response to stresses.

The published data on expression of various MT-like genes from a variety of plant species, is summarized in Table 1.

TABLE 1

Metallotheionein-like gene products identified in plants and their expression patterns. (+) indicates up-regulation, (−) down-regulation and (+/−) no change in preferentially expressed tissue except as cited in parenthesis. ABA, absicisic acid; $GA_3$, gibberellic acid.

| MT-like gene products | Transcript accumulation | Response to factors |
|---|---|---|
| CLASS I, TYPE 1 | | |
| Arabidopsis—AtMT1 | roots, seedlings | Cu, Zn, Cd (+, in leaves) |
| Canola—LSC54 | senescent leaves, flowers | — |
| Mimulus—MT | roots | Cu (+/−); Cd, Zn (−) |
| Cotton—MT1 | root | — |
| Chickpea—CanMT-1 | etiolated epicoty[1] | — |
| White cover—TrMT1B | stolon internode | — |
| Pea—PsMT$_A$ | roots, etiolated leaves | — |
| Bean—MT1a, Mt1b | root, stem, aged leaves | Cd, Cu, Zn (+/−) |
| Grass—pmcMT1 | Cu-treated shoots | Cu (+) |
| Wheat—wali1 | roots>leaves | Al (+) |
| Barley—Ids1 | Fe-deficient roots | — |
| Rice—OsMT-1 | roots, sucrose straved tissues, senescent leaves | Cu, Heat shock (+) |
| Maize—MT1 | roots | — |
| CLASS I, TYPE 2 | | |
| Citrus—CitMT36 | leaves, fruit | Zn, Cu (+/−) |
| Apple—AMT1 | flower, young fruit | cool storage (+) |
| Kiwi—pKIWI504 | roots, cell division stage fruit | — |
| Soybean—KC9-10 | leaves>roots | Cu (−) |
| Tomato—LeMTB | leaves | — |
| Castor bean—RCMIT | cotyledons | — |
| Chickpea—CanMT-2 | etiolated epicotyl | — |
| Bean—MT2 | trichromes, leaves, stem, flower | Cu, ZN, Cd, (+/−) |
| White cover—TrMT1A | stolon node | — |
| Cabbage—MT | inflorescence | — |
| Coffee—CAMETAL1 | leaves | — |
| Strawberry—FMET1 | fruit | — |
| Arabidopsis—AtMT2b | leaves | Cu, Cd, Zn (+, in seedlings) |
| Tomato—LeMT-A | leaves>roots | — |
| Tobacco—MT | leaves | wound (+), Cu (+) |
| Elder—JET12 | leaflets | abscission, ethylene |
| Rice—Ose712, OsMT-2 | embryos, sucrose straved tissue | — |
| Rice—RicMT | stems>shoots, roots | Cu, Zn, Cd, Fe, Pb, Al (+, in shoots) (−, in roots) |
| Barley—B22E | embryos, aleurone layer | ABA, GA3 (+/−) |
| CLASS I, TYPE 3 | | |
| Papaya—MT | ripe fruit | — |
| Citrus—CitMT45 | fruit | Zn, Cu (+/−) |
| Kiwi—pKIWI503 | ripe fruit | — |
| Apple—AMT2 | fruit, aged leaves | cool storage (+) |
| Raspberry—RAS2 | ripening fruit | — |
| Strawberry—MT | ripening fruit | — |
| Cherry—PAMT1 | fruit | — |
| Arabidopsis—AtMT3 | leaves | — |
| Banana—pBAN3-6 | fruit, leaves | — |
| Rice—EST | — | — |
| White spruce—EMB30 | somatic embryos, leaves | — |
| CLASS II | | |
| Soybeen—MT | cotyledons | — |
| Arabidopsis | dry seeds | — |
| Wheat—EcI | embryos | ABA (+); Zn (−) |
| Maize—pMEC | embryos | ABA (+) |

From the data in Table 1, it is clear that each MT-like gene type exhibits characteristic developmental and tissue-specific expression patterns. The expression of class II MT genes, such as for the wheat and maize EcMT, is restricted to immature embryos (Kawashima et al., *Euro. J. Biochem.* 209:971–976, 1992; White and Rivin, *Plant Physiol.* 108:831–832, 1995; Reynolds and Crawford, *Plant Mol. Biol.* 32:823–829, 1996). Type 1 MT-like transcripts have been detected primarily in roots (de Miranda et al., *FEBS Lett.* 260:277–280, 1990; Evans et al., *FEBS Lett.* 262:29–32, 1990; Zhou and Goldsbrough, *Plant Cell* 6:875–884, 1994; Hsieh et al., *Plant Mol. Biol.* 32:525–529, 1996) and senescent leaves (Buchanan-Wollaston, *Plant Physiol.* 105:839–846, 1994, Buchanan-Wollaston, *Plant Mol. Biol.* 33:821–834, 1997; Hsieh et al., *Plant Mol. Biol.* 32:525–529, 1996; Foley et al., *Plant Mol. Biol.* 33:583–591, 1997). Type 2 MT-like transcripts accumulate in the aerial portions such as leaves, stems, and flowers (Snowden and Gardner, *Plant Physiol.* 103:855–861, 1993; Foley and Singh, *Plant Mol. Biol.* 26:435–444, 1994; Coupe et al., *Planta* 197:442–447, 1995; Zhou and Goldsbrough, *Mol. Gen. Genet.* 248:318–328, 1995; Choi et al., *Plant Physiol.* 112:353–359, 1996; Whitelaw et al., *Plant Mol. Biol.* 33:503–511, 1997). Transcripts of type 3 MT-like genes have been detected in fruits, and show differential expression during fruit development (Ledger and Gardner,

*Plant Mol. Biol.* 25:877–886, 1994; Lam and Abu Baker, *Plant Physiol.* 112:1735, 1996; and Reid and Ross, *Physiologia Planatrum* 100:183–189, 1997). Type 3 MT-like transcripts are also present in leaves (Dong and Dunstan, *Planta* 199:459–466, 1996; Bundithya and Goldsbrough, *Plant Physiol.* 114:S-251, 1997; Clendennen and May, *Plant Physiol.* 115:463–469, 1997). Some class I MT genes show programmed expression during embryogenesis. Transcripts of barley pZE40, rice Ose712 (both type 2) and white spruce EMB30 (type 3) genes are expressed temporally during embryo maturation (Smith et al., *Plant Mol. Biol.* 20:255–266, 1992; Chen and Chen, *Plant Physiol.* 114:1568, 1997; and Dong and Dunstan, *Planta* 199:459–466, 1996).

SUMMARY

The invention provides, inter alia, an isolated promoter (as defined herein) from a metallothionein-like gene (i.e., the "dfMTP" promoter; SEQ ID NO: 17). The promoter is useful for expressing heterologous proteins either transiently in host cells or transgenically in stably transformed cells. The dfMTP promoter (SEQ ID NO: 17) can allow for developmental-specific expression of genes placed under its control.

Another aspect of the invention provides fragments and deletions of the promoter, such as those shown in SEQ ID NOS: 22, 23, 24, 25, and variants thereof. The variant promoters are characterized by their retention of at least 50% sequence identity with the disclosed promoter sequences (SEQ ID NOS: 17, 22, 23, 24, and 25), or by their retention of at least 20, 30, 40, 50, or 60 consecutive nucleic acid residues of the disclosed promoter sequences (SEQ ID NOS: 17, 22, 23, 24, and 25). In each case these promoters at least retain promoter activity and, in some cases, these promoters exhibit native dfMTP promoter activity.

It is also contemplated that promoters such as the CaMV35S promoter may be altered through the introduction of one or more sequences found in the dfMTP promoter. The resulting promoter is characterized by its retention of at least 20, 30, 40, 50, or 60 consecutive nucleic acid residues of the disclosed promoter sequences (SEQ ID NOS: 17, 22, 23, 24, and 25).

Another aspect of the invention provides vectors containing the above-described promoters and variants thereof. The vectors can be transformed into host cells. In some cases the resulting host cell can give rise to a transgenic plant.

The invention also provides transgenes. These transgenes include one of the above-described promoter sequences operably linked to one or more open reading frames (ORFs). The transgenes can be cloned into vectors and subsequently used to transform host cells, such as bacterial, insect, mammalian, fungal, yeast, or plant cells.

Accordingly, the invention provides transgenic plants such as maize, wheat, rice, millet, tobacco, sorghum, rye, barley, brassica, sunflower, seaweeds, lemna, oat, soybean, cotton, legumes, rape/canola, alfalfa, flax, sunflower, safflower, brassica, cotton, flax, peanut, and clover; lettuce, tomato, cucurbits, cassava, potato, carrot, radish, pea, lentil, cabbage, cauliflower, broccoli, Brussel sprouts, peppers and other vegetables; citrus, apples, pears, peaches, apricots, walnuts, and other fruit trees; orchids, carnations, roses, and other flowers; cacao; poplar, elms, and other deciduous trees; pine, Douglas-fir, spruce, and other conifers; turf grasses; cacao; and rubber trees and other members of the genus Hevea.

In yet another embodiment, the invention provides methods for expressing certain proteins in host cells, such as plant host cells. Such methods involve operably linking a promoter, such as a promoter as summarized above, to at least one ORF to produce a transgene, and introducing the transgene into a plant. Accordingly, the invention also provides proteins that are produced by these methods.

The promoters also can be characterized by analyzing various promoter elements found within the promoter sequence. Hence, the invention also provides promoters that maintain promoter activity and include at least eight promoter elements selected from the group consisting of E-box motifs (SEQ ID NO: 1), ERE elements (SEQ ID NO: 20), AT-rich regions (SEQ ID NO: 3), MRE elements (SEQ ID NO: 21), and ACGT core elements (SEQ ID NO: 4), and duplicates thereof, wherein the promoter displays promoter activity.

The invention also provides promoters that contain the following promoter elements in the following order: 3'-ERE element (SEQ ID NO: 20), AT-rich region (SEQ ID NO: 3), ERE element (SEQ ID NO: 20), ERE element (SEQ ID NO: 20), E-box motif (SEQ ID NO: 1), MRE element (SEQ ID NO: 21), ACGT core element (SEQ ID NO: 4), ACGT core element (SEQ ID NO: 4), and ACGT core element (SEQ ID NO: 4)-5'.

The invention also provides vectors, host cells, and transgenic plants that include a promoter as described above by their inclusion of various promoter elements.

The invention also provides methods for conferring developmental-specific expression of a gene to a plant. The method involves operably linking an ORF to a dfMTP promoter or variant there of (summarized above) to produce a transgene. The transgene is then transformed into a host cell, and the cell is regenerated into a plant.

These and other aspects of the invention will be readily apparent upon reading the following detailed description.

BRIEF DESCRIPTION OF THE FIGURES

FIG. 1 shows the genomic sequence of a metallothionein-like gene obtained from Douglas-fir, and its endogenous promoter (dfMTP promoter).

SEQUENCE LISTING

Figure 2:
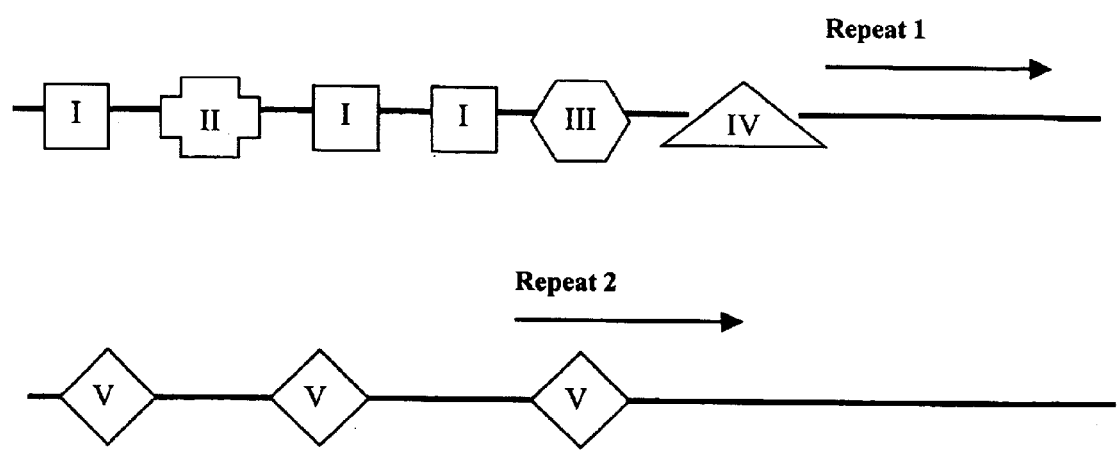
FIG. 2 is a schematic diagram of the dfMTP promoter. The promoter elements are identified as follows: I denotes an ERE element; II denotes an AT-rich region; III denotes an E-box region; IV denotes a MRE element; and V denotes an ACGT-core region. The arrows indicate the approximate locations of the repeat elements. The line connecting the elements together represents a nucleic acid strand, and regions of the line located between the elements represent respective inter-element spaces.

The nucleic and amino acid sequences listed in the accompanying sequence listing are shown using standard letter abbreviations for nucleotide bases, and three-letter code for amino acids. Only one strand of each nucleic acid sequence is shown, but the complementary strand is understood to be included by any reference to the displayed strand.

SEQ ID NO: 1 is the nucleic acid sequence of an E-box motif.

SEQ ID NO: 2 is the nucleic acid sequence of a RY-repeated element.

SEQ ID NO: 3 is the nucleic acid sequence of an AT-rich region.

SEQ ID NO: 4 is the nucleic acid sequence of an ACGT-core element

SEQ ID NO: 5 is the nucleic acid sequence of an opaque-2-like binding site.

SEQ ID NOs: 6 and 7 are nucleic acid sequences of respective conserved gymnosperm-like regions.

SEQ ID NO: 8 is the nucleic acid sequence of a TATA box.

SEQ ID NO: 9 is the nucleic acid sequence of a CAAT box.

SEQ ID NO: 10 is the nucleic acid sequence of an entire gPmMTα gene, including an untranslated region (UTR) and promoter.

SEQ ID NO: 11 is a cDNA sequence derived from the gPmMTa gene.

SEQ ID NO: 12 is the 3'-untranslated region (UTR) of the gPmMTα gene.

SEQ ID NO: 13 is the predicted amino acid sequence of the Douglas-fir metallothionein-like protein (MT-like protein).

SEQ ID NOs: 14 and 15 are specific examples of respective opaque-2 like binding sites.

SEQ ID NO: 16 is a nucleic acid sequence found 5' to the initiation start codon of the gPM2S1 gene.

SEQ ID NO: 17 is the nucleic acid sequence of the naturally occuring dfMTP promoter.

SEQ ID NOs: 18 and 19 are G Box-like motifs.

SEQ ID NO: 20 is the nucleic acid sequence of an ethylene response element (ERE).

SEQ ID NO: 21 is the nucleic acid sequence of a metal response element (MRE).

SEQ ID NO: 22 is the nucleic acid sequence of the pMTP0.9 promoter construct.

SEQ ID NO: 23 is the nucleic acid sequence of the pMTP0.7 promoter construct.

SEQ ID NO: 24 is the nucleic acid sequence of the pMTP0.5 promoter construct.

SEQ ID NO: 25 is the nucleic acid sequence of the pMTP0.2 promoter construct.

SEQ ID NOs: 26 and 27 are the nucleic acid sequences of two respective 150-bp direct repeats.

SEQ ID NO: 28 is a Douglas-fir nuclear-protein binding site.

DETAILED DESCRIPTION

I. Definitions

Unless otherwise noted, technical terms are used according to conventional usage. Definitions of common terms used in molecular biology may be found in Lewin, *Genes VII*, Oxford University Press, 1999 (ISBN 0-19-879276-X); Kendrew et al. (eds.), *Encyclopedia of Molecular Biology*, Blackwell Science Ltd., 1994 (ISBN 0-632-02182-9); and Meyers (ed.), *Molecular Biology and Biotechnology: A Comprehensive Desk Reference*, VCH Publishers, Inc., 1995 (ISBN 1-56081-569-8).

In order to facilitate review of the various embodiments of the invention, the following definitions of terms is provided:

"cDNA (complementary DNA)." A "cDNA" is a piece of DNA lacking internal, non-coding segments (introns) and transcriptional regulatory sequences. cDNA also may contain untranslated regions (UTRs) that are responsible for translational control in the corresponding RNA molecule. cDNA is usually synthesized in the laboratory by reverse transcription from messenger RNA extracted from cells.

"Cationic Peptides." "Cationic peptides" are endogenous antimicrobial peptides produced by plants and animals typically consisting of 12–45 amino acids. Additionally, they are amphipathic molecules having a net positive charge (cationic) at physiological pH. Although cationic antimicrobial peptides (CAPs) are structurally diverse, they fall into two general classes of structures: α-helical peptides, such as the cecropins and magainans, and β-sheet peptides stabilized by intramolecular disulphide bonds, such as the defensins, protegrins, and tachyplesins. Hancock and Lehrer, *Trends Biotechnol.* 16:, 1998; Zasloff, *Curr. Opin. Immunol.* 4:3–7, 1992; Cociancich et al., *Biochem. J.* 300:567–575 1994; and Piers and Hancock, *Mol. Microbiol.* 12:951–958, 1994. Natural CAPs vary greatly in their respective spectra of biological activities, including killing bacteria (Gram-positive and -negative), fungi, protozoa, and even viruses. CAPs normally kill susceptible microorganisms in vitro at concentrations from 0.25 µg/mL to 4 µg/mL (Hancock and Lehrer, *Trends Biotechnol.* 16:, 1998), providing exciting possibilities in the face of the declining efficacy of conventional antibiotics. Furthermore, the expression of CAPs in plants may introduce broad-spectrum resistance to phytopathogenic microorganisms. Jaynes, *Plant Science* 89:43–53, 1993; and Misra and Zhang, *Plant Physiol.* 106:977–981, 1994.

Cationic peptides are one type of protein that may be expressed under control of the disclosed dfMTP promoter (SEQ ID NO: 17). Other proteins that confer disease resistance, resistance to environmental stress, resistance to insect infestation, herbicide resistance, or enhanced consumer-related traits, for example, flavor, odor, or color, may be expressed under the control of the dfMTP promoter (SEQ ID NO: 17) described herein.

"Deletion." A "deletion" is the removal of one or more nucleic acid residues from DNA sequence, the regions on either side of the removed sequence being joined together.

"Douglas-fir Metallothionein-like (dfMTP) promoter." The nucleic acid sequence of the dfMTP promoter is provided in SEQ ID NO: 17. However, the invention also encompasses variants and fragments of the dfMTP promoter that are characterized by their ability to exhibit at least promoter activity, and in some cases additionally exhibit native dfMTP promoter activity. These variants have at least 50%, 60%, 70%, 80%, or 90% sequence identity when compared to the nucleic acid sequence shown in SEQ ID NO: 17. These variants can be isolated from nature using the hybridization or PCR techniques described below, or they can be made by manipulating the nucleic acid sequence shown in SEQ ID NO: 17.

The dfMTP promoter shown in SEQ ID NO: 17 contains several distinct promoter elements and inter-element spaces that are arranged in series in the DNA fragment. One or more of these elements or inter-element spaces can be altered, deleted, and/or duplicated without loss of promoter activity. Also, one of ordinary skill in the art will appreciate that any of various other promoter elements can be added to the promoter shown in SEQ ID NO: 17 without loss of promoter activity and/or native dfMTP promoter activity. Hence, the invention provides promoters that maintain native promoter activity and/or promoter activity and include at least 10, 12, 14, 16, 18, 20, 22, 30, or 35 of the promoter elements contained within the dfMTP promoter (SEQ ID NO: 17).

Variants of the dfMTP promoter also can be characterized by the number of contiguous nucleic acid residues they share with the dfMTP promoter (SEQ ID NO: 17). For example a variant of the dfMTP promoter can share at least 20, 25, 30, 40, 50, or 60 contiguous nucleic acid residues with the dfMTP promoter shown in SEQ ID NO: 17. Such variants additionally will be characterized by their ability to drive the expression of a transgene operably linked to it.

"Insertion." An "insertion" is the addition of a nucleotide or an amino acid residue into a nucleic acid sequence or an amino acid sequence.

"Isolated." An "isolated" biological component (such as a nucleic acid or protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term "isolated" also embraces nucleic acids and proteins prepared by recombinant expression in a host cell as well as chemically synthesized nucleic acids.

"Native dfMTP Promoter Activity." Native "dfMTP promoter activity" is characterized by developmental-specific transcription as illustrated by the results shown in Table 2. The dfMTP promoter has been shown to drive transcription in tissue from Douglas-fir stage-5 megagametophyte tissue to a greater extent than in stage-6 megagametophyte tissue. Hence, the dfMTP promoter shows developmental-specific activity. "Developmental-specific activity" is defined as the ability of a promoter to drive a higher level of transcription in one tissue during one-stage development when compared to transcription in the same tissue during a different stage in development.

Furthermore, developmental-specific expression can be determined by creating transgenic plants and assaying the resulting transgenic tissues (e.g., leaves, flowers, seeds, roots) for transgene mRNA. Developmental-specific expression is then quantified by comparing the level of mRNA expressed in one tissue at one time point to the level expressed in the same tissue at a later time point. The degree of developmental-specific expression is expressed in terms of a percentage of expression, i.e., the percentage of mRNA in one tissue at a specific time compared to the same tissue at a different time point. For example, 100% (1x) expression denotes that an equal amount of expression is seen in two different stages of development, and 200% (2x) denotes that twice as much mRNA is expressed at one stage compared to another stage. Native dfMTP promoter activity is, therefore, defined by the ability of the dfMTP promoter to drive a higher expression of mRNA during one stage of development compared to another stage of development in tissue derived from the same plant (i.e., at least 101%). Of course, the dfMTP promoter can exhibit an even stronger bias for developmental-specific expression, such as at least 125%, 150%, 200%, 250%, or 300% developmental-specific expression.

"Oligonucleotide ("oligo")." An "oligonucleotide" refers to a linear polynucleotide sequence of up to about 100 nucleotide bases in length.

"Open reading frame (ORF)." An "open reading frame" is a series of nucleotide triplets (codons) coding for amino acids without any internal termination codons. These sequences are usually translatable into a peptide.

"Operably linked." A first nucleic acid sequence is "operably linked" with a second nucleic acid sequence when even the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

"Orthologs." "Orthologs" are nucleic acid or amino acid sequences that share a common ancestral sequence and that diverged when a species carrying that ancestral sequence split into two species. Orthologous sequences are usually also homologous sequences.

"Probes and primers." Nucleic acid "probes and primers" may be prepared based on the nucleic acid sequences provided by this invention. A "probe" comprises an isolated nucleic acid sequence attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al. (eds.), *Molecular Cloning: A Laboratory Manual*, 2nd ed., vols. 1–3, Cold Spring Harbor Laboratory Press, Cold Spring Harbor, N.Y., 1989; and Ausubel et al. (eds.), *Current Protocols in Molecular Biology*, Greene Publishing and Wiley-Interscience, New York (with periodic updates), 1987.

"Primers" are short nucleic acids, preferably DNA oligonucleotides 15 nucleotides or more in length, that are annealed to a complementary target DNA strand by nucleic acid hybridization to form a hybrid between the primer and the target DNA strand, then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

As noted, probes and primers are preferably 15 nucleotides or more in length, but, to enhance specificity, probes and primers of 20 or more nucleotides may be preferred.

Methods for preparing and using probes and primers are described, for example, in Sambrook et al: (eds.), *Molecular Cloning: A Laboratory Manual*, 2nd ed., vols. 1–3, Cold Spring Harbor Laboratory Press, Cold Spring Harbor, N.Y., 1989; Ausubel et al. (eds.), *Current Protocols in Molecular Biology*, Greene Publishing and Wiley-Interscience, New York (with periodic updates), 1987; and Innis et al., *PCR Protocols: A Guide to Methods and Applications*, Academic Press: San Diego, 1990. PCR primer pairs can be derived from a known sequence, for example, by using computer programs intended for that purpose such as Primer™ (Version 0.5, 1991, Whitehead Institute for Biomedical Research, Cambridge, Mass.). One of skill in the art will appreciate that the specificity of a particular probe or primer increases with the length of the probe or primer. For example, a primer comprising 20 consecutive nucleotides will anneal to a target with a higher specificity than a corresponding primer of only 15 nucleotides. Thus, in order to obtain greater specificity, probes and primers may be selected that comprise, by way of example, 10, 20, 25, 30, 35, 40, 50 or more consecutive nucleotides.

"Promoter Activity." "Promoter activity" is defined as the ability of a DNA sequence to drive transcription (serve as the initiation site for transcription). Promoter activity varies with the number and position of promoter elements (defined below). For example, the dfMTP promoter can be altered such that it loses its developmental-specific activity (native activity), but yet maintains its ability to drive transcription.

"Promoter elements." "Promoter elements" as used herein refers to sub-domains within the promoter that function to confer developmental-specific expression, serve to enhance expression, or serve to inhibit expression. A promoter can contain a multiplicity of promoter elements. Furthermore, some elements can appear more than once within a single promoter. Examples of such elements are E-box motifs (SEQ ID NO: 1), RY-repeat elements (SEQ ID NO: 2), AT-rich regions (SEQ ID NO: 3), ACGT-core elements (SEQ ID NO: 4), Opaque-2-like elements (SEQ ID NO: 5), and conserved gymnosperm-like regions (SEQ ID NOS: 6 and 7). Additional examples of promoter elements can be found in U.S. Pat. No. : 5,723,751 to Chua; U.S. Pat. No. 5,608,149 to Barry et al.; U.S. Pat. No. 5,589,615 to De Clercq et al.; U.S. Pat. No. 5,589,583 to Klee et al.; U.S. Pat. No. 5,677,474 to Rogers; U.S. Pat. No. 5,487,991 to Vandekerckhove et al.; and U.S. Pat. No. 5,530,194 to Knauf et al. Typically, a TATA box is found on the 3'-end of a series of promoter elements.

Examples of specific promoter elements are provided above and in the sequence listing. However, one of skill in the art will appreciate that the specific examples shown in the sequence listing can be modified while still maintaining promoter activity. For example, a base in an RY-repeat element can be altered by the substitution of one or more nucleic acid residues while maintaining the functionality of the RY-repeat element within the overall promoter sequence.

After a promoter has been identified, the promoter elements can be characterized, such as is described below for the dfMTP promoter (SEQ ID NO: 17; and FIG. 1). This promoter contains a series of identifiable promoter elements. These elements appear in series in the genomic DNA, as is shown schematically in FIG. 2. The space between the elements is hereinafter referred to as "inter-element space." An inter-element space can be modified by the addition, deletion, and/or substitution of nucleotides without loss of promoter activity.

The dfMTP promoter also can be modified by deleting elements from the promoter and/or duplicating elements within the promoter. One of ordinary skill in the art will appreciate that such modifications to the promoter can enhance promoter activity, inhibit promoter activity, or alter the level of developmental-specific expression of the promoter.

One of skill in the art also will appreciate that, by modifying the order of the promoter elements, the number of the promoter elements, and/or the length of the inter-element space(s) in a promoter, one can modify the activity and/or native dfMTP activity of the promoter. However, in each case, the dfMTP promoter will retain an driving the expression of the gene that is operably linked to it. Assays for quantifying dfMTP activity as well as native dfMTP activity are provided below.

"Protein." A biological molecule expressed by a gene and comprised of amino acids.

"Purified." The term "purified" does not require absolute purity; rather, it is intended as a relative term. Thus, for example, a purified protein preparation is one in which the protein referred to is purer than in its natural environment within a cell or within a production reaction chamber (as appropriate).

"Recombinant." A "recombinant" nucleic acid includes a sequence that is not naturally occurring or, includes a sequence made by an artificial combination of two otherwise separate sequences. This artificial combination is often accomplished by chemical synthesis or, more commonly, by an artificial manipulation of isolated segments of nucleic acids, e.g., by genetic engineering techniques.

"Sequence identity." The term "sequence identity" is used to describe a similarity between two nucleic acid sequences or between two amino acid sequences. Sequence identity typically is expressed in terms of percentage identity; the higher the percentage, the more similar the two sequences.

Methods for aligning sequences for comparison purposes are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad Sci. USA* 85:2444–2448, 1988; Higgins and Sharp, *Gene* 73:237–244, 1988; Higgins and Sharp, CABIOS 5:151–153, 1989; Corpet et al., *Nucleic Acids Res.* 16:10881–10890, 1988; Huang et al., *Computer Applications in the Biosciences* 8:155–165, 1992; and Pearson et at., *Methods Mol. Biol.* 24:307–331, 1994. Altschul et al., *J. Mol. Biol.* 215:403–410, 1990, presents a detailed consideration of sequence-alignment methods and homology calculations.

The NCBI Basic Local Alignment Search Tool (BLASTs, Altschul et al. *J. Mol. Biol.* 215:403–410, 1990) is available from several sources, including the National Center for Biotechnology Information (NCBI, Bethesda, Md.) and on the Internet, for use in connection with the sequence-analysis programs blastp, blastn, blastx, tblastn and tblastx. BLAST™ can be accessed at the web site maintained by the NCBI. A description of how to determine sequence identity using this program also is available at the web site.

For comparisons of amino acid sequences of greater than about 30 amino acids, the "Blast 2 sequences" function in the BLAST™ program is employed using the default BLOSUM62 matrix set to default parameters, (gap existence cost of 11, and a per-residue gap cost of 1). When aligning short peptides (fewer than about 30 amino acids), the alignment should be performed using the Blast 2 sequences function, employing the PAM30 matrix set to default parameters (open gap 9, extension gap 1 penalties). Proteins having even greater similarity to the referenced sequences will show increasing percentage identities when assessed by this method, such as at least 45%, at least 50%, at least 60%, at least 70%, at least 75%, at least 80%, at least 85%, at least 90%, or at least 95% sequence identity.

A first nucleic acid is "substantially similar" to a second nucleic acid if, when optimally aligned (with appropriate nucleotide insertions or deletions) with the other nucleic acid (or its complementary strand), nucleotide sequence identity occurs in at least about 60%, 75%, 80%, 85%, 90%, or 95% of the nucleotide bases (as used herein, "optimally aligned" sequences exhibit a maximal possible sequence identity). Sequence similarity can be determined by comparing the nucleotide sequences of two nucleic acids using the BLAST™ sequence-analysis software (blastn) available from The National Center for Biotechnology Information. Such comparisons may be made using the software set to default settings (expect=10, filter=default, descriptions=500 pairwise, alignments=500, alignment view=standard, gap existence cost=11, per residue existence=1, per residue gap cost=0.85). Similarly, a first polypeptide is substantially similar to a second polypeptide if the polypeptides show sequence identity of at least about 75%–90% or greater when optimally aligned and compared using BLAST™ software (blastp) using default settings.

"Transformed." A "transformed" cell is a cell into which a nucleic acid molecule has been introduced by molecular biology techniques. As used herein, the term "transformation" encompasses all techniques by which a nucleic acid molecule might be introduced into such a cell, including transfection with a viral vector, transformation with a plasmid vector, and introduction of naked DNA by electroporation, lipofection, floral dip, and particle gun acceleration.

"Transgenic plant." As used herein a "transgenic plant" refers to a plant that contains recombinant genetic material ("transgene") not normally found in a wild-type plant of the same species. Thus, a plant that is grown from a plant cell into which recombinant DNA is introduced by transformation is a transgenic plant, as are all offspring of that plant that contain the introduced transgene (whether produced sexually or asexually).

"Vector." A "vector" is a nucleic acid molecule as introduced into a host cell, with the intention of producing a transformed host cell. A vector may include one or more nucleic acid sequences, such as an origin of replication, that permit the vector to replicate in the host cell. A vector also may include one or more selectable marker genes and other genetic elements known in the art.

Unless otherwise defined, all technical and scientific terms used herein have the same respective meanings as commonly understood by one of ordinary skill in the art to which this invention belongs. Although methods and materials similar or equivalent to those described herein can be used in the practice or testing of the present invention, suitable methods and materials are described below. In case of conflict, the present specification, including definitions, will control. In addition, the materials, methods, and examples are illustrative only and are not intended to be limiting.

Moreover throughout the specification the singular terms "a", "an", and "the" include plural referents unless context clearly indicates otherwise.

II. Isolation and Analysis of Promoter Activity

A. Cloning of a Douglas-fir Metallothionein-like Gene

A Douglas-fir genomic library constructed in the λEMBL3 bacteriophage was screened with a PM2.1 cDNA probe (Chatthai et al., *Plant Mol. Biol.* 34:243–254, 1997). From approximately 1×10$^6$ genomic clones, three clones (λPMMTa, λPMMTb, λPMMTc, respectively) strongly hybridized to the PM2.1 probe. Southern hybridization of λDNA isolated from these clones with the PM2.1 cDNA probe revealed that they had different restriction maps, and corresponded to different MT-like genes in Douglas-fir. The genomic clone λPMMTa, containing an insert of about 20 kb, was selected for further analysis. A 4.5-kb XbaI fragment of λPMMTa was subcloned into a pUC19 plasmid, giving rise to the gPmMTα genomic clone.

B. Characterization of the Douglas-fir gPmMTa Gene

The nucleotide sequence of 2.3 kb of gPmMTα (SEQ ID NO: 10) and the deduced primary structure of a Douglas-fir MT-like protein (MT-like protein; SEQ ID NO: 13) are shown in FIG. 1. Comparison of the nucleotide sequences of gPmMTα gene (SEQ ID NO: 10) and PM2.1 cDNA indicated that the gPmMTα the gene includes three exons interrupted by two introns respectively located at amino acid positions 17 and 39. The first and the second introns are 125 and 78 bp in length, respectively. Both regions exhibit characteristics of putative plant introns such as the A/T abundance, the :GU . . . AG: boundary, and the consensus YUNAN (where Y is C or U, and N is any nucleotide) branchpoint sequence (Brown et al., *Plant Mol. Biol.* 32:531–535, 1996). The coding region of the gPmMTα gene (SEQ ID NO: 10) was not identical to that of the PM2.1 cDNA; however, they shared high respective degrees of similarities at both the nucleotide (94%) and amino acid (98.5%) levels.

Primer-extension assay using total RNA from stage-5 megagametophyte and the 23-mer oligonucleotide 5'-PMMT, complimentary to the 5'-terminus of the PM2.1 coding sequence, was performed to locate the transcription-start site. The longest transcript, as deduced from the sequence ladder produced using the same primer, was initiated from a cytosine, located 92 nucleotides upstream from the ATG initiation codon. Based on the primer-extension assays, the transcription-start site at the cytosine was denoted the start site and designated "+1."

Promoter-sequence data are now available for genes for class I MT-like proteins from pea (Evans et al., *FEBS Lett.* 262:29–32, 1990), tomato (Whitelaw et al., *Plant Mol. Biol.* 33:503–511, 1996), and *Arabidopsis* (Zhou and Goldsbrough, *Mol. Gen. Genet.* 248:318–328, 1995), and barley (Klemdal et al., *Mol. Gen. Genet.* 228:9–16, 1991), and for genes for class II MT-like proteins from wheat (Kawashima et al., *Euro. J. Biochem.* 209:971–976, 1992) and maize (de Framond, *FEBS Lett.* 290:103–106, 1991). When the dfMTP was compared with the analogous regions of these genes using the CLUSTALV program (Higgin and Sharp, *Computer App. Bio. Sci.* 5:151–153, 1989), no significant similarity between dfMTP and any other sequences could be detected. However, a number of cis-regulatory motifs common to these genes were evident in the Douglas-fir dfMTP upstream of the putative TATA box (FIGS. 1 and 2). These motifs include an E-box (CANNTG; SEQ ID NO: 1; Stalberg et al., *Planta* 199:515–519, 1996) at position −493, three copies of palindromic G-box-like motifs (AACGTT, CACGTG; SEQ ID NOs: 18 and 19, respectively, Foster et al., *FASEB J.* 8:192–200, 1994) between position −104 and −165, and three copies of putative ethylene-responsive elements (AWTTCAAA; SEQ ID NO: 20; Montgomery et al., *Proc. Nat. Acad Sci. USA* 87:1406–1410, 1993) around positions −580, −590, and −745, respectively. The gPmMTα gene (SEQ ID NO: 10) also contains a motif similar to the core metal-responsive element (MRE) (TGCRCNC; SEQ ID NO:21; Thiele, *Nucl. Acids Res.* 20:1183–1192, 1992). The MRE motif has been found only in pea PsMT$_A$ (Fordham-Skelton et al., *Plant Mol. Biol.* 34:659–668, 1997). A unique and interesting feature found in the proximal 5'-upstream sequence of the Douglas-fir gPmMTα gene (SEQ ID NO: 10) is the presence of two 150-bp direct-repeat units (−134/+20 and −34/−175 regions, respectively; SEQ ID NOS: 26 and 27, respectively). Both sequences contain the putative TATA-box and identical sequences flanking the predicted transcriptional start site. It is unknown whether transcription is initiated from the distal TATA-box.

C. Analysis of the dfMTP Promoter-glucuronidase Chimeric Gene Activity in Douglas-Fir and Transgenic Tobacco Functional analyses of the promoter of the Douglas-fir MT-like gene was performed using intact and deleted gPmMTα promoter sequences fused to the β-glucuronidase (uidA or GUS) coding region. The fusion gene constructs either were assayed in Douglas-fir seeds transiently transformed using a particle bombardment or stably introduced into tobacco plants via *Agrobacterium tumefaciens*.

Using the particle bombardement method, a 0.9-kb gPmMTα promoter/uidA chimeric construct (pMTP0.9; SEQ ID NO: 22), a promoter-less reporter gene (pBI101), and the CaMV 35S promoter/uidA gene (pBI221) construct were delivered into developing Douglas-fir megagametophytes, immature zygotic embryos, and mature somatic embryos. GUS activity was determined as GUS-expression units (GEUs) appearing as blue spots after performing the histochemical GUS assay two days after bombardment. Bombardment with the pBI101 produced no visible GUS transient expression. By contrast, GUS activity was evident whenever Douglas-fir tissues were bombarded with one or the other of pBI221 and pMTP0.9 (SEQ ID NO: 22). The efficiency of the 0.9-kb gPmMTα promoter compared to the constitutive CaMV 35S promoter was estimated by counting the number of GEUs per tissue. As shown in Table 2, bombardment with the pMTP0.9 construct (SEQ ID NO: 22) produced 2- to 3-fold higher GEUs in both megagametophytes and zygotic embryos than the pBI221 plasmid. Although individual GEUs on somatic embryos bombarded with pMTP0.9 (SEQ ID NO: 22) were too densely arranged to count, the somatic embryos bombarded with pBI221 appeared to have lower density of GEUs. The results indicated that the dfMTP is capable of driving expression of GUS in megagametophytes, zygotic embryos, and somatic embryos of Douglas-fir.

Figure 3:
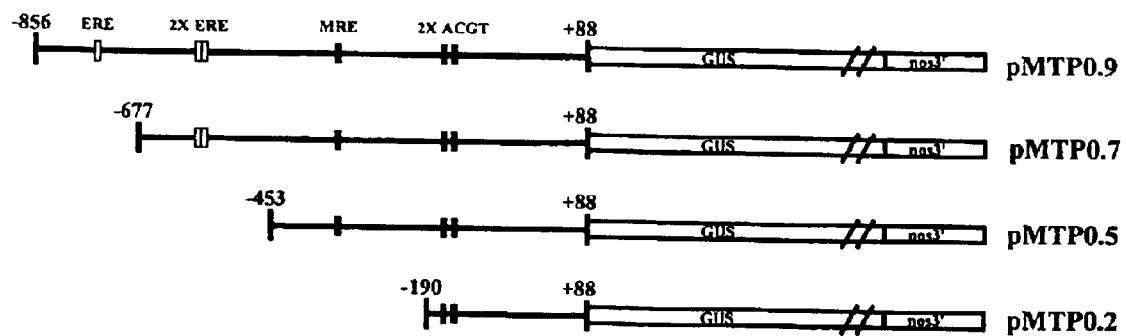
FIG. 3 shows a schematic of various dfMTP-promoter deletion mutants.

To localize regulatory regions responsible for expression of MT-like genes in Douglas-fir, a series of deletion mutants of the gPmMTα gene promoter were constructed having varying lengths of promoter sequences. Four 5'-deletion dfMTP promoter fragments were separately linked to the uidA gene (with nos terminator) in pUC19-based vectors (pBI221). The resulting constructs were designated pMTP0.9 (SEQ ID NO: 22), pMTP0.7 (SEQ ID NO: 23), pMTP0.5 (SEQ ID NO: 24), and pMTP0.2 (SEQ ID NO: 25) (FIG. 3). All constructs included the 5'-UTR of the transcript and the initiation codon of gPmMTα. Each construct was assayed by transient expression after particle bombardment into stage-5 and staged megagametophytes, stage-6 zygotic embryos, and mature somatic embryos of Douglas-fir. The results of three assays per construct are shown in Table 2 below.

TABLE 2

| Construct | GEUs per tissue (mean ± SE) | | |
| --- | --- | --- | --- |
| | Stage-5 megagametophyte | Stage-6 megagametophyte | Stage-6 zygotic embryos |
| pBI221 | 24 ± 5 a | 16 ± 2 a | 4 ± 0.6 a |
| pMTP0.9 | 80 ± 3 c | 33 ± 1 b | 9 ± 0.9 b |
| pMTP0.7 | 84 ± 2 c | 33 ± 3 b | 19 ± 1.0 c |
| pMTP0.5 | 37 ± 3 a | 13 ± 2 a | 3 ± 0.0 a |
| pMTP0.2 | 44 ± 4 b | 13 ± 2 a | 9 ± 0.3 b |
| pBI101 | nil | nil | nil |

Table 2 sets forth the results from assays involving ten megagametophytes or embryos in each of three bombardments. For each replicate, the number of GUS-transient expression units (GEUs) were scored and averaged out as GEUs per tissue. The average numbers of GEUs per tissue were calculated from three independent bombardments. The respective standard errors of means are indicated. Significant treatment effects (P<0.05) between constructs were calculated by separate one-way ANOVA. For experiments using the same tissue type, the identical letter (e.g., a, b, or c) indicates no significant difference between the two constructs with respect to the effect on transient GUS activity.

The pMTP0.9 construct (SEQ ID NO: 22; −856/+88; FIG. 3) generated approximately 80 and 33 GEUs per tissue in stage-5 and 6-megagametophytes, respectively. No significant difference in GUS activity was observed when the tissues were bombarded with the pMTP0.7 construct (SEQ ID NO: 23; −677/+88; FIG. 3). Deletion constructs according to pMTP0.5 (SEQ ID NO: 24; pMTP0.5; FIG. 3) and mMTP0.2 (SEQ ID NO:25; pMTP0.2; FIG. 3) consistently produced only 50% of the GUS expression generated by pMTP0.9 (SEQ ID NO: 22) and pMTP0.7(SEQ ID NO: 23), respectively. The −677/−453 region of the gPmMTa gene contains a positive regulatory element(s) for expression in megagametophytes.

In stage-6 zygotic embryos, the pMTP0.7 construct (SEQ ID NO: 23) produced the highest GUS activity (19 GEUs per embryo), which accounted for 2-fold higher activity than observed with the pMTP0.9 construct (SEQ ID NO: 22). The pMTP0.5 construct (SEQ ID NO: 24) generated only 3 GEUs per embryo; however, the pMTP0.2 construct caused a 3-fold increase in GUS activity relative to the pMTP0.5 construct (SEQ ID NO: 24). This is in contrast to what was found in megagametophytes the respective efficiencies of pMTP0.5 (SEQ ID NO: 24) and pMTP0.2 (SEQ ID NO: 25) were similar. These observations indicate that the −677/−453 region of the gPmMTα gene promoter is essential for high-level gene expression in zygotic embryos. In contrast, the −853/−677 and −453/−190 regions may contain negative regulatory elements. GUS activity was evident in somatic embryos of all constructs studied; however, with the exception of pMTP0.5 (SEQ ID NO: 24), GEUs generated were too densely arranged to count.

In stable-transformation studies, four 5'-deletion fragments of the dfMTP promoter (SEQ ID NO: 17) were fused to the GUS-coding region in the binary vector pBI121. The chimeric genes were introduced into tobacco plants via Agrobacterium-mediated transformation. The chimeric gene integration and the number of uidA gene copies in the transformed tobacco were verified using PCR-amplification and Southern blot analysis, respectively. Histochemical staining for GUS activity in developing seeds of the transgenic tobacco, XBY3-118 (which contains the pMTP0.9 (SEQ ID NO: 22) construct) revealed very low or no GUS activity. Little to no GUS activity also was observed in embryos, endosperms, leaves, and roots of the transgenic tobacco. However, it is likely that by modifying the promoter structure transcription activity will be increased.

III Implications of Results

In an attempt to identify promoter regions responsible for the regulated expression of the gPmMTα (SEQ ID NO: 10) gene, chimeric genes containing a series of promoter deletions fused to the uidA reporter gene were constructed and introduced in to cells of immature seeds and somatic embryos of Douglas-fir by particle bombardment. The promoter activity was examined in transient GUS expression assays. Results (summarized in Table 2) showed that a sequence of 190 base pairs upstream of the gPmMTα transcription-start site is sufficient to direct GUS expression in megagametophyte tissue, zygotic embryos, and somatic embryos of Douglas-fir. The proximal 190-bp sequence, in addition to a putative TATA box sequence, contains an inverted repeat of ACGT-core motif (SEQ ID NO: 4). The core sequence is part of the G-box (CACGTG; SEQ ID NO: 19), which appears to be conserved in the promoters of active MT-like genes identified so far, including Arabidopsis MT1α (Zhou and Glodsbrough, *Mol. Gen. Genet.* 248:318–328, 1995), pea PsMTα (Fordham-Skelton et al., *Plant Mol. Biol.* 34:659–668, 1997), tomato LeMT$_B$ (Whitelaw et al., *Plant Mol. Biol.* 33:503–511, 1997), and rice rgMT (Hsieh et al., *Plant Mol. Biol.* 28:381–389, 1995). In wheat, the presence of the core sequence (as part of ABRE) in the 5'-flanking region of the EcMT gene was implicated in ABA-induced gene expression in germinating embryos (Kawashima et al., *Euro. J. Biochem.*

209:971–976, 1992). The core sequence is absent in the promoter of non-functional Arabidopsis MT1b (Zhou and Goldsbrough, *Mol. Gen. Genet.* 248:318–328, 1995). The G-box and related sequences are required for the differential expression of genes by stress, light, abscisic acid (Busk and Pagè, *Plant Cell* 9:2261–2270, 1997; Guilfoyle, *Genetic Engineering*, Setlow, J. K. (ed.), Plenum Press, New York, 1997; Shen and Ho, *Physiologia Plantarum* 101:653–664, 1997), and ethylene (Sessa et al., *Plant Mol. Biol.* 28:145–153, 1995). Several proteins of the bZIP family of scription factors, which bind to the ACGT-core containing motif, have been characterized (Foster et al., *FASEB J.* 8:192–200, 1994; Guiltinan et al., *Science* 250:267–271, 1990; Kawagoe and Murai, *Plant Science* 116:47–57, 1996; and Schindler et al., *Plant Cell* 4:1309–1319, 1992a). An interaction of an ACGT-core motif with another regulatory element (also called a coupling element), found in a proximal or distal distance to the ACGT-core motif, defines a regulatory complex that confers signal-response specificity of a gene (Shen and Ho, *Physiologia Plantarum* 101:653–664, 1997). As a result, the ACGT-core motifs (SEQ ID NOS: 18 AND 19) are involved in responses to various different physiological and environmental stimuli such as ABA-induced expression of barley HVA22 (Shen and Ho, *Physiologia Plantarum* 101:653–664, 1997), ABA- and water-stress induced lea-like genes of Arabidopsis (Hull et al., *Plant Science* 114:181–192, 1996), rice (Mundy et al., *Proc. Nat. Acad Sci. USA* 87:1406–1410, 1990) and wheat (Marcotte et al., *Plant Cell* 1:969–976, 1989), UV-light response of the parsley chs promoter (Block et al., *Proc. Nat. Acad Sci. USA* 87:5387–5391, 1990); and light-response of the Arabidopsis rbcS-1A gene (Donald and Cashmore, *EMBO J*. 9:1717–1726, 1990). In vitro binding of nuclear extracts from Douglas-fir seed nuclear extracts showed that nuclear proteins bound to the ATTGCAATTTCCA ACGTTG sequence (SEQ ID NO: 28) putative binding sites underlined), thus suggesting that the core motif may be a regulating component of expression of the gPmMTα gene (SEQ ID NO: 10).

The second functional domain identified in the gPmMTα promoter extends from the positions −677 to −453. This region conferred a high level of expression of the uidA gene in both megagametophyte and embryos. Sequence analysis of this region revealed the presence of several putative regulatory elements, including two copies of the ethylene-responsive element (ERE; SEQ ID NO: 20), an A/T rich region (SEQ ID NO: 3), and an E-box motif (SEQ ID NO: 1). In a number of plants, ethylene is implicated in regulating developmental-specific and developmentally regulated expression of MT-like genes. For example, MT-like cDNAs were inducted during leaf senescence in *Brassica napus* (Buchanan-Wollaston, *Plant Physiol.* 105:839–846, 1994) and Arabidopsis (Zhou and Goldsbrough, *Plant Cell* 6:875–884, 1994); during ethylene-stimulated leaf abscission in *Sambucus nigra* (Coupe et al., *Planta* 197:442–447, 1995); and during fruit-ripening in kiwi (Ledger and Gardner, *Plant Mol. Biol.* 25:877–886, 1994), apple (Reid and Ross, *Physiologia Plantarum* 100:183–189, 1997), papaya (Lam and Abu Baker, *Plant Physiol.* 112:1735, 1996), and cherry (Wiersma et al., *Plant Physiol.* 116:867, 1998). It has also been shown that activation of the glutathione-S-transferase gene occurs in response to ethylene during petal senescence, and that such activation involves the promoter element (ERE ATTTCAAA; SEQ ID NO: 20) Itzhaki et al., *Proc. Nat. Acad Sci USA* 91:8925–8929, 1994. Interestingly, the putative ERE is highly conserved in the MT-like genes of pea (Fordham-Skelton et al., *Plant Mol. Biol.* 34:659–668, 1997), tomato (Whitelaw et al., *Plant Mol. Biol.* 33:503–511, 1997), Arabidopsis (Zhou and Goldsbrough, *Mol. Gen. Genet.* 248:318–328, 1995), and Douglas-fir (described herein).

In gene-transfer studies, deletion of the PsMT$_A$ promoter fragment containing three copies of ERE caused deficiency in expression of a reporter gene within roots and senescent aerial tissues of transgenic Arabidopsis (Fordham-Skelton et al., *Plant Mol. Biol.* 34:659–668, 1997). As described herein, transient-expression assays showed that the deletion constructs lacking two copies of ERE (SEQ ID NO: 20) exhibited a significant decrease in GUS activity in developing seeds. Moreover, the existence of the three ERE (SEQ ID NO: 20) in the disclosed promoter indicates that the promoter is also likely to be induced via ethylene. The second sequence, CATTTG (SEQ ID NO: 1), at position −493 resembles the putative E-box (CANNTG; SEQ ID NO: 1). This motif was shown to be a recognition site for DNA-binding proteins in the promoter of the bean β-phaseolin gene (Kawagoe and Murai, *The Plant J.* 2:927–936, 1992), and was responsible for quantitative and correct seed-specific expression of napin genes (Ellerström et al., *Plant Mol. Biol.* 32:1019–1027, 1996; and Stålberg et al., *Planta* 199:515–519, 1996). Finally, an A/T-rich 39-bp sequence extending from −637 to −604 was identified. Previous studies of seed-specific genes have shown that A/T-rich sequences in the promoter can act as general enhancers of expression (Stålberg et al., *Planta* 199:515–519, 1996).

The 5'-flanking region of gPmMTα contains a putative metal regulatory element (MRE), suggesting the possibility of metal-regulated transcription of this gene. This is in agreement with the results from northern analyses showing metal-induced (i.e., zinc, iron, copper, and manganese) accumulation of PM2.1 transcripts in seeds and young seedlings of Douglas-fir. To date, there have been only two reports of the existence of MRE, in plant MT-like genes. The pea PsMT$_A$ (Fordham-Skelton et al., *Plant Mol. Biol.* 34:659–668, 1997) and tomato LeMT$_B$ (Whitelaw et al., *Plant Mol. Biol.* 33:503–511, 1997) each contain one putative MRE in the 5'-flanking region of the genes; however, there is no evidence that the sequence is functional. Sequences exactly matching the consensus sequence for either the core MREs or the upstream activation sequences (UASs) of yeast CUP1 are not present within the MT-like genes of maize (de Framond, *FEBS Lett.* 290:103–106, 1991), Arabidopsis (Zhou and Goldsbrough, *Mol. Gen. Genet.* 248:318–328, 1995), and cotton (Hudspeth et al., *Plant Mol. Biol.* 31:801–705, 1996), despite evidence that their expression is modulated by metal ions. The UAS of CUP1 was placed upstream a of a reporter gene and introduced into tobacco (Mett et al., *Proc. Nat. Acad Sci. USA* 90:4567–4571, 1993). Transcription of this gene was dependent upon the introduction of ACE1 (yeast transcription factor; de Framond, *FEBS Lett.* 290:103–106, 1991; Kawashima et al., *Euro. J. Biochem.* 209:971–976, 1992; and Zhou and Goldsbrough, *Mol. Gen. Genet.* 248:318–328, 1995), which binds to the UASs, indicating that tobacco lacks proteins capable of stimulating transcription from fungal UASs. MREs distinct from those of animals and fungi have yet to be described within plant MT-like genes.

Studies on promoters for plant MT-like genes using stable transformation have been limited. The pea type-MT-like PsMT$_A$ gene promoter directed GUS expression in Arabidopsis root tissues except the root apex (Fordham-Skelton et al., *Plant Mol. Biol.* 34:659–668, 1997). In cotton, GUS fused to the MT1-A promoter showed the highest GUS activity in the root tip (Hudspeth et al., *Plant Mol. Biol.* 31:701–705, 1996). GUS-expression analysis in transgenic Arabidopsis showed that the promoter of the *Brassica napus* LSC54 gene was highly induced during leaf senescence and in response to wounding and pathogen infection (Butt et al., *Plant J.* 16:209–221, 1998). The barley B22EL8 gene promoter sequence directed the expression of a reporter gene in barley embryos but was not functional in transgenic tobacco (Klemsdal et al., *Mol. Gen. Genet.* 228:9–16, 1991). The data described herein shows that the gPmMTα promoter was active in Douglas-fir, but did not express GUS at a detectable level in transgenic tobacco. Although gene silencing cannot be excluded, it seems unlikely because all of the transgenic tobacco lines were equally affected. Thus, the absence of detectable GUS activity could be due to a lack or a very low level of transcription of the gPmMTα promoter-uidA chimeric gene. However, it is predicted that, through modification (i.e., deletion and/or addition) of the promoter elements in the dfMTP promoter, expression will be observed in tobacco. However, this expression may not be developmental-specific.

IV. Alteration of Promoter Structure

A. Modifications of the Douglas-fir Metallothionein-like Protein (dfMTP) Promoter The structure of a given promoter determines the level of mRNA expression as well as the tissue/developmental-specificity of the promoter. However, expression levels and tissue/developmental-specificity can be maintained when deletions, substitutions, and/or additions are made to the promoter sequence. Hence the scope of the invention encompasses dfMTP promoters that have been modified through the incorporation of deletions, substitutions, and/or additions. However, regardless of the number of mutations that are incorporated into the dfMTP promoter, the promoters continue to maintain dfMTP promoter activity, or native dfMTP promoter activity, as described above.

One possible method for modifying the dfMTP promoter is by inserting additional promoter elements into the promoter sequence. For example, the promoter can be modified such that an E-box motif (SEQ ID NO: 1), RY-repeated element (SEQ ID NO:2), AT-rich region (SEQ ID NO: 3), ACGT-core element (SEQ ID NO: 4), opaque-2-like binding site (SEQ ID NO: 5), a MRE (SEQ ID NO: 21); an ERE element (SEQ ID NO: 20), G-box motif(SEQ ID NOS: 18 and 19), and/or a conserved gymnosperm-like region (SEQ ID NOS: 5 and 6) is added. One of skill in the art will appreciate that standard molecular biology techniques can be used to insert one or more of these elements into the promoter sequence. The modified promoter then can be transiently transfected into gymnosperm, monocot, or dicot tissue and the tissue tested for transgene expression.

Similarly, one or more promoter elements can be deleted from the subject promoter sequences. The resulting modified promoter can be tested for transcriptional activity and developmental-specificity. Given the disclosure herein of the dfMTP promoter, it also is possible to make both additions and deletions and to test for promoter activity.

Finally, the dfMTP promoter also can be modified such that the inter-element spaces contain one or more deletions, insertions, and/or substitutions. One of ordinary skill in the art can use standard molecular biology techniques to insert one or more additional nucleic acid residues into the inter-element spaces, delete one or more nucleic acid residues from the inter-element spaces, and/or substitute one or more other sequences into the inter-element spaces. However, regardless of the number and combination of insertions, deletions, and substitutions, the sequence continues to display promoter activity or native dfMTP promoter activity as provided above.

B. Methods for Producing Douglas-fir Metallothionein-like Promoters, Variants, and Deletion Mutants thereof

1. Cloning Nucleic Acid Sequences Encoding the dfMTP Promoter

Provided with the nucleic acid sequence of the dfMTP promoter (SEQ ID NO: 17), one of ordinary skill in the art will appreciate that several different methods can be used to isolate the Douglas-fir dfMTP promoter (SEQ ID NO: 17). One example of such a method is the polymerase chain reaction (PCR) (U.S. Pat. No. 4,683,202 to Mullis; and Saiki et al., *Science* 239:487–491, 1988). Once isolated, the dfMTP promoter (SEQ ID NO: 17) sequence is useful for driving the expression of transgenes.

When using PCR to isolate a sequence encoding the gene, a first primer can be designed that targets the extreme 5'-end of the sequence, and a second primer can be designed that targets the extreme 3'-end of the sequence. These primers can be used such that they generate multiple copies of the promoter sequence. The copies are isolated by separation on an agarose gel. The fragment of interest then is removed from the gel and ligated into an appropriate vector.

Alternatively, the promoter can be created by engineering synthetic strands of DNA that partially overlap each other (Beaucage and Caruthers, *Tetrahedron Lett.* 22:1859–1869, 1981; and Matthes et al., *EMBO. J.* 3:801–805, 1984). The synthetic strands are annealed, and a DNA polymerase is used to fill in the single-stranded regions. The resulting synthetic double-stranded DNA molecule can be cloned into a vector.

For use as primers and probes, nucleic acid sequences can contain at least 15, 20, 30, 40, 50, or 60 contiguous nucleic acid residues of the sequence shown in SEQ ID NO: 17 or the complementary strand of the molecule shown in SEQ ID NO: 17. The nucleic acid sequences are useful for performing hybridization protocols, such as northern blots or Southern blots as described in Sambrook et al. (eds.), *Molecular Cloning, A Laboratory Manual*, 2d ed., vols. 1–3, Cold Spring Harbor Laboratory Press, Cold Spring Harbor, N.Y., 1989.

These hybridization protocols can be used to identify nucleic acid sequences that are substantially similar to the sequence shown in SEQ ID NO: 17. A successful hybridization to such a sequence indicates that the analogous nucleic acid sequence hybridizing to the oligonucleotide probe comprises at least a fragment of the sequence shown in SEQ ID NO: 17. Generally, hybridization conditions are classified into categories, for example very high stringency, high stringency, and low stringency. The conditions corresponding to these categories for probes of approximately 600 bp are provided below.

| Very High Stringency (detects sequences that share 90% sequence identity) | | | | | |
|---|---|---|---|---|---|
| Hybridization | in | 5× | SSC at | 65° C. | 16 hours |
| Wash twice | in | 2× | SSC at | room temp. | 15 minutes each |
| Wash twice | in | 0.2× | SSC at | 65° C. | 20 minutes each |

-continued

High Stringency
(detects sequences that share 80% sequence identity or greater)

| Hybridization | in | 3× | SSC | at | 65° C. | 16 hours |
| Wash twice | in | 2× | SSC | at | room temp. | 15 minutes each |
| Wash twice | in | 0.5× | SSC | at | 55° C. | 20 minutes each |

Low Stringency
(detects sequences that share greater than 50% sequence identity)

| Hybridization | in | 3× | SSC | at | 65° C. | 16 hours |
| Wash twice | in | 2× | SSC | at | room temp. | 20 minutes each |

Variant dfMTP-promoter (SEQ ID NO: 17) sequences may be produced by standard DNA-mutagenesis techniques, for example, M13 primer mutagenesis. Details of these techniques are provided in Sambrook et al. (eds.), *Molecular Cloning: A Laboratory Manual*, 2nd ed., vol. 1–3, Ch. 15, Cold Spring Harbor Laboratory Press, Cold Spring Harbor, N.Y., 1989; and Ausubel et al. (eds.) *Current Protocols in Molecular Biology*, Greene Publishing and Wiley-Interscience, New York (with periodic updates), 1987. By the use of such techniques, variants may be created that differ slightly from the dfMTP promoter sequences specifically disclosed, yet that still encode a promoter having promoter activity. DNA molecules and nucleotide sequences that are derivatives of those specifically disclosed herein and that differ from those disclosed by the deletion, addition, or substitution of nucleotides while still maintaining promoter activity and/or native dfMTP promoter activity are comprehended by this invention.

2. Transformation

The DNA constructs of the invention, containing a dfMTP promoter (SEQ ID NO: 17) operably linked to one or more transgenes, may be either homologous or heterologous to a host cell. If homologous to the host cell, i.e., if the transgene is produced by the host cell in nature, the construct may be connected operably to a different secretory signal sequence and/or terminator sequence than in the natural environment. In this context, the term "homologous" is intended to include a cDNA sequence encoding a transgene native to the host cell. The term "heterologous" is intended to include a transgene not expressed by the host cell in nature. Thus, the DNA sequence may be from a different organism, or it may be a synthetic sequence.

A host cell according to the invention, into which the DNA construct or the recombinant expression vector of the invention is to be introduced, may be any cell capable of driving expression of the dfMTP promoter (SEQ ID NO: 17). Such cells include bacteria cells, yeast cells, fungal cells, insect cells, plant cells, and other higher eukaryotic cells.

Various methods of introducing the DNA construct into host cells are well known in the art. For example, in some species, the Ti plasmid of *A. tumefaciens* can be used to transform host cells (Gouka et al., *Nature Biotech.* 6:598–602, 1999). The host cell also can be transformed using gene blasting techniques (described above) and standard chemical treatments.

IV. EXAMPLES

The following non-limiting examples are provided to illustrate particular features of the present invention. The scope of the present invention is not limited to those features exemplified.

Materials and Methods

Douglas-fir Genomic DNA Preparation

Spring-flush needles of Douglas-fir were used for isolation of high-molecular-weight genomic DNA according to De Verno et al. (De Verno et al., *Canadian Forestry Service Publication* PI-X-88, 1989) with some modifications. Fifty grams of needles were surface-sterilized, ground to a fine powder in liquid nitrogen, and mixed with 400 mL of cold extraction buffer (50 mM Tris-HCl pH 8.0, 5 mM EDTA, 0.35 M sorbitol, 0.1% BSA, 10% PEG, 0.1% spermine, 0.1% spermidine and 0.1% β-mercaptoethanol). The mixture was filtered through cheese cloth and miracloth. The pellet was recovered by centrifugation at 9000 rpm for 15 min and resuspended in 50 mL of wash buffer (50 mM Tris-HCl pH 8.0,25 mM EDTA, 0.35 M sorbitol, 0.1% β-mercaptoethanol). The solution was mixed with 10 mL of 5% sarcosyl, 7 mL of 5M NaCl, and 5 mL of 8.6% cetyltrimethylammonium bromide (CTAB) in 0.7 M NaCl, and incubated at 60° C. for 15 min. The mixture was extracted with chloroform:isoamyl alcohol (24:1, v/v). The DNA was precipitated with 2 volumes of cold ethanol and collected by centrifugation. The DNA pellet was washed with 70% cold ethanol and gently dissolved in TE buffer.

Construction of a Douglas-fir Genomic Library

A Douglas-fir genomic library was constructed according to the protocol for the lambda EMBL3/Bam HI vector kit (Stratagene, La Jolla, Calif.). Briefly, Douglas-fir genomic DNA was isolated from spring-flush needles as described above, and purified by ultracentrifugation through a CsCl gradient (Sambrook et al. (eds.), *Molecular Cloning: A Laboratory Manual*, 2nd ed., vols. 1–3, Cold Spring Harbor Laboratory Press, Cold Spring Harbor, N.Y., 1989). The DNA was partially digested with Sau3AI, and DNA fragments ranging from 9 to 20 kb were purified from a 0.7% low-melting-point agarose gel. The size-selected DNA fragments were treated with calf intestine alkaline phosphatase (CIAP), ligated into BamHI half-site arms of λEMBL3 according to manufacturer's instructions (Stratagene), and packaged in vitro into phage particles using the Gigapack II® packaging system (Stratagene). A titer for the stored Douglas-fir genomic library was 6×10$^{10}$ pfu/mL.

Screening of the Douglas-fir Genomic Library

The Douglas-fir genomic DNA library was plated with *E. coli* XL 1-Blue MRA cells (600 μL of OD$_{600}$=0.5 in 10 mM MgSO$_4$) on NZY plates at approximately 5×10$^4$ pfu per 150×15 mm plate. Plaque lifting, membrane preparation, prehybridization, hybridization and membrane washing were performed using a PM2.1 cDNA insert as a probe to isolate the metallothionein-like protein gene. After secondary screening, recombinant genomic lambda clones were amplified and stored as phage stocks at 4° C.

DNA Sequence Analysis

DNA sequences were determined from both strands by the dideoxynucleotide chain termination method using Sequenase™ version 2.0 (United States Biochemical, Cleveland, Ohio). Commercially available and custom-synthesized primers were used.

For each reaction, 5 μg of plasmid DNA was denatured by adding 0.1 volumes of 2 M NaOH, 2 mM EDTA and incubating 30 min at 37° C. The mixture was neutralized by adding 0.1 volume of 3 M sodium acetate pH 5.2. The DNA was precipitated with 2 volumes of ethanol at −80° C. for 30 min. After centrifugation, the pelleted DNA was washed with 70% ethanol, and stored at −20° C. until further use. Annealing of the primer to the DNA template was performed in 10 μL (40 mM Tris-HCl pH 7.5, 20 mM MgCl$_2$, 50 mM NaCl, 10% DMSO, 1 pmol primer) at 37° C. for 30 min. After annealing, 3 μM each of dGTP, dCTP, and dTTP, 10 mM DDT, 5 μCi of (α-$^{35}$S) dATP (1000 Ci/mmol, DuPont), and 1 unit of Sequenase™ version 2.0 T7 DNA polymerase was added. The mixture was incubated for 2–5 min at room temperature. Aliquots of 3.5 μL of the mixture were added to four tubes containing 2.5 μL of the respective termination reaction (G, A, T or C), each containing 80 μM of each dGTP, dATP, dTTP and dCTP, 50 mM NaCl, and 8 μM of either ddGTP, ddATP, ddTTP or ddGTP. The four tubes were incubated at 37° C. for 5 min. The reactions were stopped with 4 μL of stop solution (95% formamide, 20 mM EDTA, 0.5% bromophenol blue, and 0.5% xylene cyanol). The sequencing reaction was heated at 80° C. for 2 min, and 2.5 μL of each reaction was loaded on a sequencing gel (6% acrylamide/bis-acrylamide (19:1, w/w), 7 M urea, 1× glycerol tolerance gel buffer, 1% ammonium persulfate, 0.025% TEMED). Electrophoresis was performed at 50 watts in glycerol tolerance gel buffer (0.1 M Tris, 30 mM Taurine, 0.5 mM EDTA). After electrophoresis, the gel was transferred to Whatman (Maidstone, England) 3 MM paper and vacuum dried for 2 h at 80° C. The gel was exposed to X-Omat film (Kodak, Rochester, N.Y.) at room temperature for a period ranging from overnight to 3 days.

Plant Transformation

Immature seeds corresponding to early- and mid-cotyledonary stages were collected on separate days. The seeds were surface-sterilized in 1% sodium hypochlorite for 5 min and rinsed 3 times in sterilized water before megagametophytes and zygotic embryos were separated. Aseptically germinated 4-week-old seedlings were used as the source of needles and roots. All samples were placed on BM-3 medium (Gupta and Pullman, U.S. Pat. No. 5,036,007, 1991) in a 60-mm-diameter Petri dish and used for particle bombardment.

Construction of GUS Expression Vectors

Douglas-fir gene promoter-GUS chimeric constructs as shown in FIG. 3 were constructed. For construction of pMTP0.9-GUS, the 0.9-kb fragment of the 5'-flanking sequence of the gPmMTα gene was PCR-amplified from the plasmid gPMMTa-Exo1.2 using a pair of primers, creating PstI/SalI sites at 5'-end and XbaI/BamHI sites at 3'-end of the promoter fragment. After partial digestion with XbaI/PstI, the 0.96-kb PCR product was cloned into pBI221 vector (Clontech, Palo Alto, Calif.) in place of the XbaI/PstI fragment of the CaMV 35S promoter region. For construction of pMTP0.2, the plasmid pMTP0.9 was partially digested with HindIII/XbaI, and the isolated 0.28-kb fragment was cloned into pBI221 vector, thereby replacing the HindIII/XbaI fragment of the CaMV 35S promoter region.

PCR was utilized to create the promoter-deletion constructs, pMTP0.7 (SEQ ID NO: 24) and pMTP0.5 (SEQ ID NO: 25), by the selection of upstream primers. In both cases, the upstream primers (5'SSP21 and 5'SSP22) contained sequences which created a SalI site at the 5'-end of the promoter region, and the downstream primer (3'-primer) contained sequences which created XbaI/BamHI site at the 3'-end of the promoter region. After digestion with SalI/XbaI, each PCR product was cloned into the pBI101 vector that lacked a promoter. The resulting plasmids were digested with HindIII/XbaI, and the released promoter fragments were cloned into the pBI221 vector in place of the CaMV 35S promoter.

For construction of p2SSP 1.2, an approximately 1.16-kb fragment of the 5'-flanking sequence of the gPM2S1 gene was PCR-amplified from the plasmid gPM2S1-EK1.3 using a pair of primers containing HindIII and XbaI recognition sites at 5'-end and 3'-end of the promoter fragment, respectively. The PCR product was cloned between HindIII and XbaI sites of pBI 221, thereby replacing the CaMV 35S promoter.

To construct chimeric genes for use in stably transformed tobacco, each of the four promoter fragments isolated from the pBI221-recombinant plasmids was cloned between the HindIII and XbaI sites of the binary vector pBI121 (Clontech), giving rise to the chimeric constructs pMTP121-0.9 (SEQ ID NO: 22), pMTP121-0.7 (SEQ ID NO: 23), pMTP121-0.5 (SEQ ID NO: 24), and pMTP121-0.2 (SEQ ID NO: 25). Each of these constructs contained a series of deletions of the gPmMTα gene promoter.

Particle Bombardment

Particle bombardment was carried out with the PDS-1000/He Particle Delivery System (Bio-Rad Laboratories, Richmond, Calif.) according to instructions provided by the manufacturer. DNA was precipitated onto gold particles (1.5–3.0 μm diameter; Aldrich Chemicals) as described by Klein et al. (Klein et al., Proc. Nat. Acad. Sci. USA 85:4305–4309, 1988). A gold-suspension (60 mg/mL) was prepared in 50% glycerol. Fifty microliters of the suspension was aliquoted into a microcentrifuge tube to which 8 μg of promoter-GUS plasmid DNA, 50 μL of 2.5 M CaCl$_2$ and 20 μL of 0.1 M spermidine were added. All additions were made while continuously vortexing the tube. The gold particles were allowed to settle, and pelleted by a brief centrifugation. The supernatant was discarded and worked separately with 140 μL cold 70% ethanol and 140 μL cold absolute ethanol. The liquid phases were immediately removed. DNA-coated gold particles were resuspended in 100 μL absolute ethanol and aliquots of 10 μL (0.8 pg DNA associated with 0.3 mg of gold particles) were delivered to each disk and air-dried. The following parameters were used for each bombardment: the gap distance between the rupture membrane and the flying disk was 0.6 cm, the disk traveled 1.6 cm before impacting a steel stopping screen, and target tissues were placed 6.0 cm from the stopping screen and bombarded once at 1300 or 1550 psi. The sample chamber was evacuated to 20 inches of mercury and the gas-acceleration tube was pressurized with a selected helium gas pressure. Each experiment was repeated three to four times, on different days, and with freshly prepared new batches of DNA-coated gold particles. The data set forth are means of the results obtained from these repeats.

Tobacco Transformation

Each of the pBI121-recombinant plasmids were transferred from E. coli DH5α cells into Agrobacterium tumefaciens. Young leaves of Nicotiana tabacum cv. Xanthi were surface-sterilized in 1% (v/v) sodium hypochlorite for 2–5 min. and rinsed thoroughly with sterile water. Leaf discs were co-cultivated with the overnight-cultured A. tumefaciens, transferred onto Murashige and Skoog (MS) medium and incubated for 2 d at 25° C. The co-cultivated leaf discs then were transferred to a shoot-inducing medium (MS medium containing 0.01 μg/mL NAA (napthalene acetic acid), 2.0 μg/mL 6-BA (benzyladenine), 100 μg/mL kanamycin and 200 g/mL carbenicillin). Young shoots were transferred to a root-inducing medium (MS medium containing 100 μg/mL kanamycin and 200 μg/mL carbenicillin).

Regenerated plants were tested for the presence of chimeric gene constructs using PCR-amplification of genomic DNA The transgenic tobacco plants were then transferred to soil, and developing seeds were collected.

Histochemical Assay for GUS Transient Expression

Bombarded explants remained on the same plates for 24–48 h before they were subjected to GUS assay (Jefferson et al., *EMBO J.* 6:3901–3907, 1987). The tissues were immersed in 500 μL of X-gluc staining solution (2 mM X-gluc, 50 mM sodium phosphate buffer pH 7.0, 10 mM EDTA, 0.5 mM potassium ferricyanide, 0.5 mM potassium ferrocyanide, and 0.1% triton X-100) overnight at 37° C. The number of blue spots were counted and photographed under a stereo dissecting microscope.

Having illustrated and described the principles of the invention in multiple embodiments and examples, it should be apparent to those skilled in the art that the invention can be modified in arrangement and detail without departing from such principles. Therefore, the invention includes all modifications coming within the spirit and scope of the following claims.

What is claimed is:

1. A recombinant promoter, capable of driving expression of a transgene operably linked to the promoter, wherein the promoter comprises nucleotides 398–853 of SEQ ID NO: 17.

2. A vector, comprising the recombinant promoter of claim 1.

3. A host cell, comprising the vector of claim 2.

4. A transgenic plant, comprising the host cell of claim 3.

5. A transgene, comprising the promoter of claim 1 and at least one ORF operably linked to the promoter.

6. A vector, comprising the transgene of claim 5.

7. A plant cell, comprising the transgene of claim 5.

8. The transgene of claim 5, wherein the ORF encodes a cationic peptide.

9. A method for expressing at least one protein in a Douglas-fir host cell, comprising:
   introducing a transgene comprising an ORF and the recombinant promoter of claim 1 into a Douglas-fir host cell; and
   allowing the Douglas-fir host cell to produce a protein from the ORF.

10. The recombinant promoter of claim 1, wherein the promoter is expressable in gametophytic tissue.

11. The promoter of claim 1, wherein the promoter comprises nucleotides 180–853 of SEQ ID NO: 17.

12. The promoter of claim 1, wherein the promoter comprises the nucleic acid sequence shown in SEQ ID NO: 17.

* * * * *

UNITED STATES PATENT AND TRADEMARK OFFICE
CERTIFICATE OF CORRECTION

PATENT NO. : 6,759,529 B1
DATED : July 6, 2004
INVENTOR(S) : Santosh Misra and Malinee Chatthai It is certified that error appears in the above-identified patent and that said Letters Patent is hereby corrected as shown below:

Column 4,
Line 31, "there of" should be -- thereof --.

Column 5,
Lines 13 and 18, "gPmMTα" should be -- gPmMTa --.

Column 10,
Line 19, "BLASTs" should be -- BLAST$^{TM}$ --.

Column 11,
Line 46, "XbαI" should be -- XbaI --.
Lines 48, 50, 54, 55 and 63, "gPmMTα" should be -- gPmMTa --.

Column 12,
Lines 36, 43, 56 and 62, "gPmMTα" should be -- gPmMTa --.

Column 13,
Lines 7, 22 and 30, "gPmMTα" should be -- gPmMTa --.

Column 14,
Lines 18, 43 and 50, "gPmMTα" should be -- gPmMTa --.
Line 59, "MTlα" should be -- Mtla --.
Line 60, "PsMTα" should be -- PsMTa --.

Column 15,
Line 11, "scription" should be -- transcription --.
Lines 38 and 40, "gPmMTα" should be -- gPmMTa --.

Column 16,
Line 30, "gPmMTα" should be -- gPmMTa --.
Line 51, "upstream a of a" should be -- upstream of a --.

Column 17,
Lines 11 and 17, "gPmMTα" should be -- gPmMTa --.

Column 20,
Line 22, "8.0,25" should be -- 8.0, 25 --.

UNITED STATES PATENT AND TRADEMARK OFFICE
CERTIFICATE OF CORRECTION

PATENT NO. : 6,759,529 B1
DATED : July 6, 2004
INVENTOR(S) : Santosh Misra and Malinee Chatthai It is certified that error appears in the above-identified patent and that said Letters Patent is hereby corrected as shown below:

Column 21,
Line 47, "gPmMTα" should be -- gPmMTa --.

Column 22,
Line 20, "gPmMTα" should be -- gPmMTa --.
Line 39, "pg" should be -- µg --.
Line 55, "*E. coil*" should be -- *E. coli* --.
Line 65, "g/mL" should be -- µg/mL --.

Column 23,
Line 2, "DNA" should be -- DNA. --

Signed and Sealed this

Fourth Day of January, 2005

JON W. DUDAS
*Director of the United States Patent and Trademark Office*